(12) United States Patent
Kubo

(10) Patent No.: US 11,510,559 B2
(45) Date of Patent: Nov. 29, 2022

(54) ENDOSCOPE SYSTEM AND METHOD OF OPERATING THE SAME

(71) Applicant: FUJIFILM Corporation, Tokyo (JP)

(72) Inventor: Masahiro Kubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 77 days.

(21) Appl. No.: 16/868,419

(22) Filed: May 6, 2020

(65) Prior Publication Data

US 2020/0260933 A1 Aug. 20, 2020

Related U.S. Application Data

(63) Continuation of application No. PCT/JP2018/040929, filed on Nov. 5, 2018.

(30) Foreign Application Priority Data

Nov. 10, 2017 (JP) .............................. JP2017-217613

(51) Int. Cl.
*A61B 1/00* (2006.01)
*A61B 1/06* (2006.01)

(52) U.S. Cl.
CPC .......... *A61B 1/0638* (2013.01); *A61B 1/0005* (2013.01); *A61B 1/00006* (2013.01);
(Continued)

(58) Field of Classification Search
CPC ............ A61B 1/00006; A61B 1/00009; A61B 1/00039; A61B 1/00043; A61B 1/00045;
(Continued)

(56) References Cited

U.S. PATENT DOCUMENTS

2006/0209185 A1* 9/2006 Yokoi .................... A61B 34/73
348/42
2011/0317044 A1 12/2011 Ishii et al.
(Continued)

FOREIGN PATENT DOCUMENTS

CN 105407780 A 3/2016
EP 3 354 188 A1 8/2018
(Continued)

OTHER PUBLICATIONS

The extended European search report issued by the European Patent Office dated Apr. 12, 2021, which corresponds to European Patent Application No. 18877088.7 and is related to U.S. Appl. No. 16/868,419.
(Continued)

*Primary Examiner* — Michael J Carey
*Assistant Examiner* — Julianna J Nicolaus
(74) *Attorney, Agent, or Firm* — Studebaker & Brackett PC

(57) ABSTRACT

An image processing unit includes a shake amount calculation section and a static image-storage control section, and the shake amount calculation section includes a shake amount-calculation processing section and an algorithm switching section. The algorithm switching section applies an algorithm varying for each image, and selects images of which the shake amounts calculated by the shake amount-calculation processing section are small. A first image and a second image, which are selected as the images of which the shake amounts are small, are stored in a static image-storage unit. A display control unit displays static images for storage.

6 Claims, 15 Drawing Sheets

(52) U.S. Cl.
CPC .... *A61B 1/00042* (2022.02); *A61B 1/000094* (2022.02); *A61B 1/0655* (2022.02); *A61B 1/0661* (2013.01)

(58) Field of Classification Search
CPC . A61B 1/0005; A61B 1/00165; A61B 1/0638; A61B 1/0661; A61B 1/0684; A61B 1/07; H04N 5/2256; H04N 5/2258; H04N 5/2354; H04N 2005/2255
See application file for complete search history.

(56) References Cited

U.S. PATENT DOCUMENTS

| | | | |
|---|---|---|---|
| 2013/0245411 A1 | 9/2013 | Saito | |
| 2016/0156822 A1* | 6/2016 | Iwasaki | G02B 23/2461 348/68 |

FOREIGN PATENT DOCUMENTS

| | | |
|---|---|---|
| JP | H03-016470 A | 1/1991 |
| JP | 2001-218217 A | 8/2001 |
| JP | 2009-230598 A | 10/2009 |
| JP | 2012-070938 A | 4/2012 |
| JP | 2013-188364 A | 9/2013 |
| JP | 5499050 B2 | 5/2014 |
| JP | 2014-220690 A | 11/2014 |
| JP | 2014220690 A * | 11/2014 |
| JP | 2015-047402 A | 3/2015 |
| JP | 2015047402 A * | 3/2015 |
| JP | 2016-054794 A | 4/2016 |
| JP | 2016-067782 A | 5/2016 |
| WO | 2017/051455 A1 | 3/2017 |

OTHER PUBLICATIONS

The partial supplementary European search report (R. 164 EPC) issued by the European Patent Office dated Dec. 2, 2020, which corresponds to European Patent Application No. 18877088.7-1122 and is related to U.S. Appl. No. 16/868,419.
International Search Report issued in PCT/JP2018/040929; dated Jan. 15, 2019.
Written Opinion issued in PCT/JP2018/040929; dated Jan. 15, 2019.
An Office Action mailed by China National Intellectual Property Administration dated Jul. 29, 2022, which corresponds to Chinese Patent Application No. 201880072739.X and is related to U.S. Appl. No. 16/868,419; with English language translation.

* cited by examiner

ENDOSCOPE SYSTEM AND METHOD OF OPERATING THE SAME

CROSS-REFERENCE TO RELATED APPLICATIONS

This application is a Continuation of PCT International Application No. PCT/JP2018/040929 filed on 5 Nov. 2018, which claims priority under 35 U.S.C § 119(a) to Japanese Patent Application No. 2017-217613 filed on 10 Nov. 2017. The above application is hereby expressly incorporated by reference, in its entirety, into the present application.

BACKGROUND OF THE INVENTION

1. Field of the Invention

The present invention relates to an endoscope system that can efficiently display images obtained using a plurality of kinds of illumination light and having a small shake.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked by an image pickup element of the endoscope.

Further, a plurality of observation modes are provided in the endoscope system so that illumination light used to irradiate an object to be observed can be switched and image processing for the image of the object to be observed can be switched in accordance with the purpose of diagnosis. Static images are acquired at portions and the like of particular interest of images obtained in these observation modes, and are used as materials for diagnosis or the like.

For example, JP2013-188364A (corresponding to US2013/0245411A1) discloses an endoscope system that acquires static images obtained in observation modes, such as a normal observation image, an oxygen saturation image, and a blood vessel-emphasized image, after the adjustment of the exposures of the static images in a case where these static images are to be acquired. Further, JP2001-218217A discloses an image freeze device that can output image signals, which are obtained at a point of time when an operator gives a freeze instruction, as a static image having the minimum color shift. Furthermore, JP2012-070938A discloses an endoscopic image recording device that can complement deficient static images with video data after an endoscopy ends.

SUMMARY OF THE INVENTION

A static image having a small color shift or a small shake is required to be stored as disclosed in JP2001-218217A in a case where a static image is to be stored. Further, even in a case where images obtained in a plurality of observation modes corresponding to a plurality of observation modes are to be stored as static images, the color shifts or the shake amounts of the images obtained in the respective observation modes are calculated and an image of which the calculated color shift is smallest is required to be stored as a static image. However, since images obtained in the respective observation modes often have different image feature values, there is a case where color shifts or shake amounts cannot be accurately calculated in a case where similar color shift calculation processing or similar shake calculation processing is to be performed on the images obtained in the respective observation modes.

An object of the invention is to provide an endoscope system and a method of operating the endoscope system that can store an image having a small shake amount as a static image by accurately calculating the shake amount of each image in a case where a plurality of kinds of illumination light are applied while being switched and images corresponding to the plurality of kinds of illumination light are acquired.

An endoscope system according to an aspect of the invention comprises a plurality of semiconductor light sources, a light source control unit, an image acquisition unit, a static-image-acquisition instruction input unit, a shake amount calculation section, and a static image-storage control section. The plurality of semiconductor light sources emit light having wavelength ranges different from each other. The light source control unit performs control to cause the plurality of semiconductor light sources to emit a plurality of kinds of illumination light, which include first illumination light having a first light emission ratio and second illumination light having a second light emission ratio different from the first light emission ratio, while switching the plurality of kinds of illumination light according to a specific light emission order and a specific light emission period. The image acquisition unit picks up images of an object to be observed illuminated with each illumination light to acquire a plurality of images. The plurality of images include first images obtained using the first illumination light and second images obtained using the second illumination light. The static-image-acquisition instruction input unit gives a static-image-acquisition instruction to acquire static images for storage of the respective images. The shake amount calculation section calculates shake amounts of the plurality of images acquired in a specific static-image-acquisition instruction period including a timing when the static-image-acquisition instruction is given. Shake amount-calculation processing for calculating the shake amount varies for each of the images. The static image-storage control section performs control to store the plurality of images in a static image-storage unit as the static images for storage in a case where a specific condition is satisfied with regard to the shake amount.

It is preferable that spectral images having a plurality of colors are included in each of the images and the shake amount-calculation processing includes first shake amount-calculation processing for calculating the first shake amount from a spectral image, which has a first color, of the first images, and second shake amount-calculation processing for calculating the second shake amount from a spectral image, which has a second color different from the first color, of the second images.

It is preferable that the first illumination light includes more light, which has a short wavelength, than the second illumination light, and the first color is a blue color and the second color is a green color.

It is preferable that the plurality of images are acquired as image sets in the specific static-image-acquisition instruction period and the static image-storage control section stores an image set, which satisfies the specific condition, as the static images for storage.

It is preferable that the image set satisfying the specific condition is an image set of which a representative shake amount, which is a sum of shake amounts of the respective images of the image set, is smallest among the plurality of image sets.

It is preferable that the static image-storage control section respectively stores a first image having the smallest shake amount with regard to the first images and a second image having the smallest shake amount with regard to the second images, among the plurality of images obtained in the specific static-image-acquisition instruction period, as the static images for storage.

It is preferable that the endoscope system further comprises a display control unit displaying the plurality of images on a display unit while switching the plurality of images according to a display condition including a specific display order and/or a specific display time, and the static image-storage control section associates the display condition with the static images for storage and stores the display condition.

Further, an endoscope system according to another aspect of the invention comprises: a plurality of semiconductor light sources that emit light having wavelength ranges different from each other; a light source control unit that performs control to cause the plurality of semiconductor light sources to emit a plurality of kinds of illumination light, which include first illumination light having a first light emission ratio and second illumination light having a second light emission ratio different from the first light emission ratio, while switching the plurality of kinds of illumination light according to a specific light emission order and a specific light emission period; an image acquisition unit that picks up images of an object to be observed illuminated with each illumination light to acquire a plurality of images, the plurality of images including first images obtained using the first illumination light and second images obtained using the second illumination light; a video storage section that stores videos of the plurality of images acquired in a specific period as temporarily stored videos; a static-image-acquisition instruction input unit that gives a static-image-acquisition instruction to acquire static images for storage of the respective images; a shake amount calculation section that calculates a shake amount of the temporarily stored video including the image acquired at a timing when the static-image-acquisition instruction is given, in which shake amount-calculation processing for calculating the shake amount varies for each of the images; and a static image-storage control section that performs control to store the plurality of images in a static image-storage unit as the static images for storage in a case where a specific condition is satisfied with regard to the shake amount.

Furthermore, an endoscope system according to another aspect of the invention comprises: a plurality of semiconductor light sources that emit light having wavelength ranges different from each other; a light source control unit that performs control to cause the plurality of semiconductor light sources to emit a plurality of kinds of illumination light, which include first illumination light having a first light emission ratio and second illumination light having a second light emission ratio different from the first light emission ratio, while switching the plurality of kinds of illumination light according to a specific light emission order and a specific light emission period; an image acquisition unit that picks up images of an object to be observed illuminated with each illumination light to acquire a plurality of images, the plurality of images including first images obtained using the first illumination light and second images obtained using the second illumination light; a static-image-acquisition instruction input unit that gives a static-image-acquisition instruction to acquire static images for storage of the respective images; a shake amount calculation section that calculates shake amounts of the plurality of images acquired in a specific period, in which shake amount-calculation processing for calculating the shake amount varies for each of the images; and a static image-storage control section that performs control to store the plurality of images in a temporary static-image-storage section as static images for temporary storage in a case where a specific condition is satisfied with regard to the shake amount, and performs control to store the static images for temporary storage in a static image-storage unit as the static images for storage, according to the static-image-acquisition instruction.

It is preferable that the specific period is a period up to a point of time dating back from a current point of time by the specific period.

Moreover, a method of operating an endoscope system according to another aspect of the invention comprises a light source control step, an image acquisition step, a static-image-acquisition instruction step, a shake amount calculation step, and a static image storage step. In the light source control step, a light source control unit performs control to cause a plurality of semiconductor light sources, which emit light having wavelength ranges different from each other, to emit a plurality of kinds of illumination light, which include first illumination light having a first light emission ratio and second illumination light having a second light emission ratio different from the first light emission ratio, while switching the plurality of kinds of illumination light according to a specific light emission order and a specific light emission period. In the image acquisition step, an image acquisition unit picks up images of an object to be observed illuminated with each illumination light to acquire a plurality of images, and the plurality of images include first images obtained using the first illumination light and second images obtained using the second illumination light. In the static-image-acquisition instruction step, a static-image-acquisition instruction input unit gives a static-image-acquisition instruction to acquire static images for storage of the respective images. In the shake amount calculation step, a shake amount calculation section calculates shake amounts of the plurality of images acquired in a specific static-image-acquisition instruction period including a timing when the static-image-acquisition instruction is given, and shake amount-calculation processing for calculating the shake amount varies for each of the images. In the static image storage step, a static image-storage control section stores the plurality of images in a static image-storage unit as the static images for storage in a case where a specific condition is satisfied with regard to the shake amount.

According to the invention, it is possible to store an image having a small shake amount as a static image by accurately calculating the shake amount of each image in a case where a plurality of kinds of illumination light are applied while being switched and images corresponding to the plurality of kinds of illumination light are acquired.

BRIEF DESCRIPTION OF THE DRAWINGS

FIG. 13 is a diagram showing a relationship among a static-image-acquisition instruction, the calculation of shake amounts, the storage of static images, and the like.

FIG. 15 is a diagram showing a relationship among a static-image-acquisition instruction, the calculation of shake amounts, the storage of static images, and the like.

FIG. 17 is a diagram showing a relationship among a static-image-acquisition instruction, the calculation of shake amounts, the storage of static images, and the like.

DESCRIPTION OF THE PREFERRED EMBODIMENTS

First Embodiment

Figure 1:
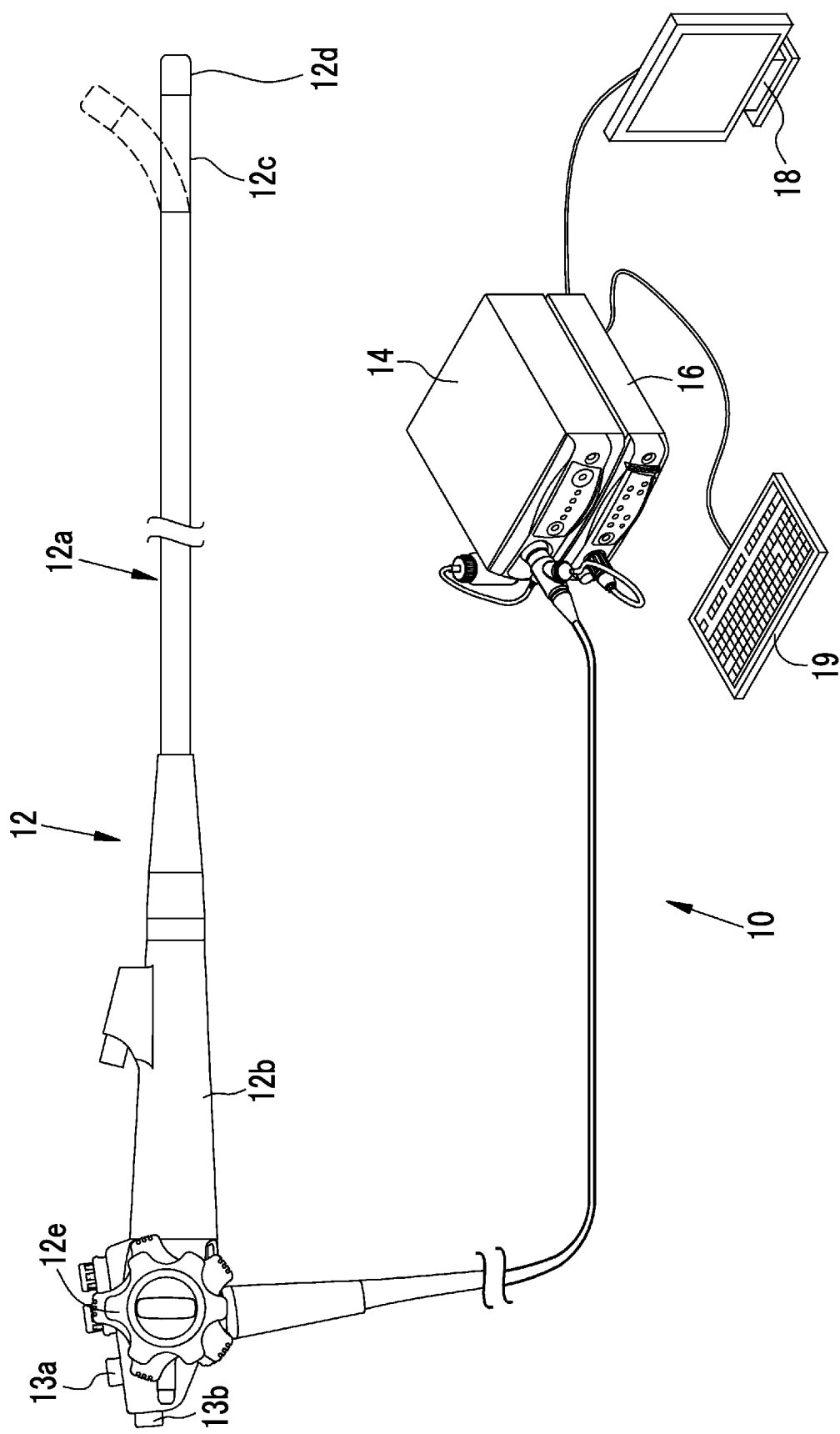
FIG. 1 is a diagram showing the appearance of an endoscope system.

As shown in FIG. 1, an endoscope system 10 according to a first embodiment includes an endoscope 12, a light source device 14, a processor device 16, a monitor 18, and a keyboard 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d faces in a desired direction. The keyboard 19 is an example of input means, and a mouse and the like (not shown) are included in addition to a keyboard shown in FIG. 1 as the input means and performs the reception, change, input, and the like of an operation and the like as with the keyboard 19.

Further, the operation part 12b is provided with a static-image-acquisition instruction SW 13a and a mode changeover SW 13b in addition to the angle knobs 12e. The static-image-acquisition instruction SW 13a is a scope switch that is used to store an image as a static image in a case where a region of interest and the like are present in an object to be observed, and is an example of a static-image-acquisition instruction input unit.

A foot switch (not shown) may be used as the static-image-acquisition instruction input unit, which is used to store an image as a static image, in addition to the static-image-acquisition instruction SW 13a. Furthermore, a plurality of kinds of illumination light are automatically switched in this embodiment, but the operation part 12b is provided with the mode changeover SW 13b that is used to manually switch the plurality of kinds of illumination light. In a case where a user detects a portion deemed to be effective for diagnosis, the user can also alternately operate the static-image-acquisition instruction SW 13a and the mode changeover SW 13b.

In this embodiment, a multi-observation mode is used as an observation mode using a plurality of kinds of illumination light. The multi-observation mode is a mode where a first image and a second image obtained on the basis of the emission of two kinds of illumination light having wavelength ranges different from each other are automatically switched and displayed on the monitor 18. The first image is an image where superficial blood vessels (first blood vessel) are emphasized. The second image is an image where deep blood vessels (second blood vessel) are emphasized. A normal observation mode or other observation modes can also be used in addition to these observation modes. The normal observation mode is a mode where a normal image is displayed on the monitor 18. The switching of the observation modes is performed by the mode changeover SW 13b provided on the operation part 12b of the endoscope.

The processor device 16 is electrically connected to the monitor 18 and the keyboard 19. The monitor 18 outputs and displays image information and the like. The keyboard 19 functions as a user interface (UI) that receives an input operation, such as function settings. An external recording unit (not shown), which records image information and the like, may be connected to the processor device 16.

Figure 2:
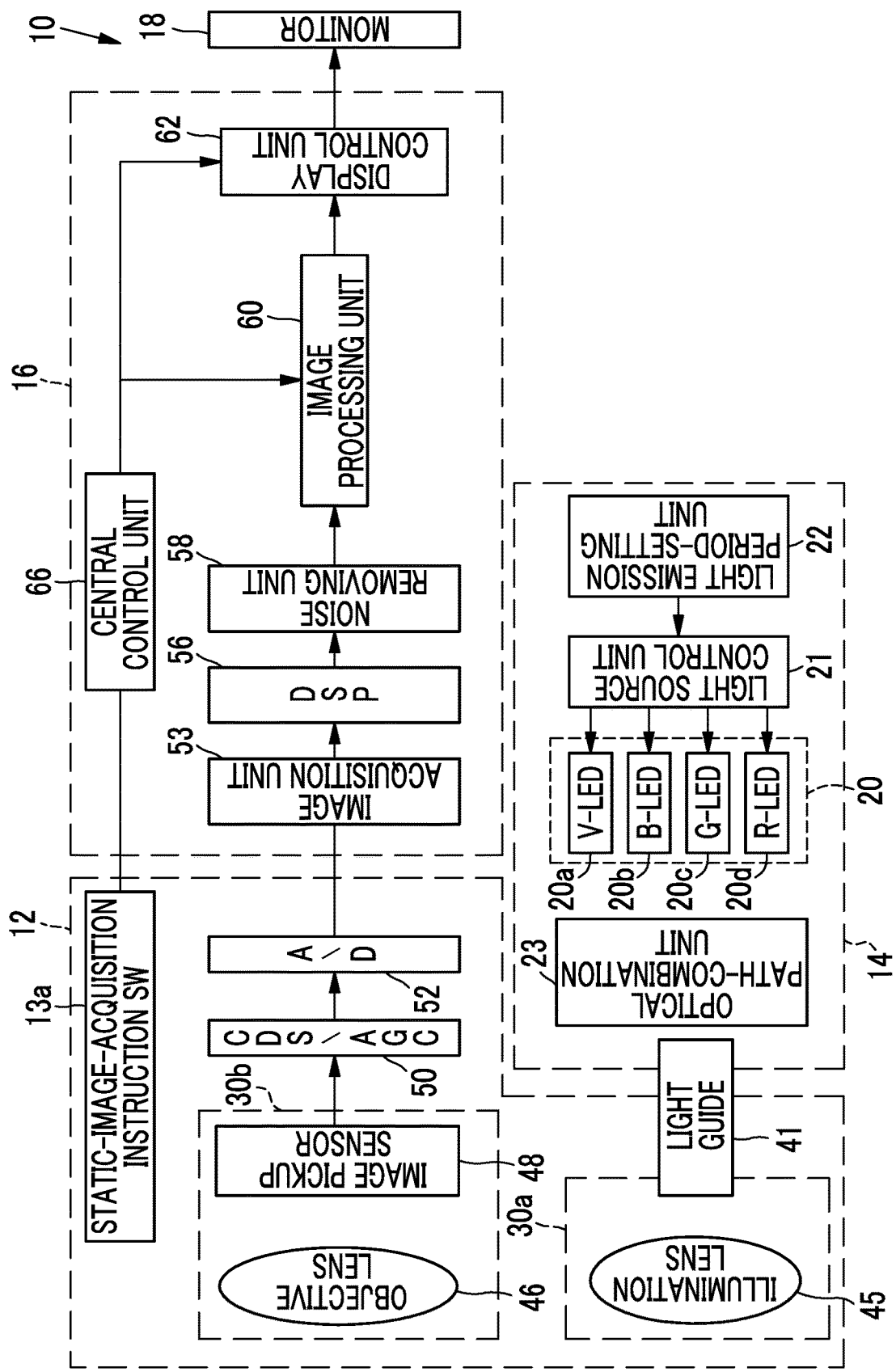
FIG. 2 is a block diagram of the endoscope system.

As shown in FIG. 2, the light source device 14 includes a light source unit 20, a light source control unit 21, a light emission period-setting unit 22, and an optical path-combination unit 23. The light source unit 20 can emit light having a plurality of wavelength ranges different from each other. In this specification, "light having a plurality of wavelength ranges different from each other" means that the plurality of wavelength ranges may partially overlap with each other without meaning that the plurality of wavelength ranges do not overlap with each other at all. The light source unit 20 includes a violet light emitting diode (V-LED) 20a, a blue light emitting diode (B-LED) 20b, a green light emitting diode (G-LED) 20c, and a red light emitting diode (R-LED) 20d to emit light having a plurality of wavelength ranges. A laser diode (LD) may be used instead of the LED.

The light source control unit 21 controls the drive of the LEDs 20a to 20d. The optical path-combination unit 23 combines the optical paths of pieces of light that are emitted from the four color LEDs 20a to 20d and have four colors. The inside of an object to be examined is irradiated with the pieces of light, which are combined by the optical path-combination unit 23, through a light guide 41 inserted into the insertion part 12a and an illumination lens 45.

Figure 3:
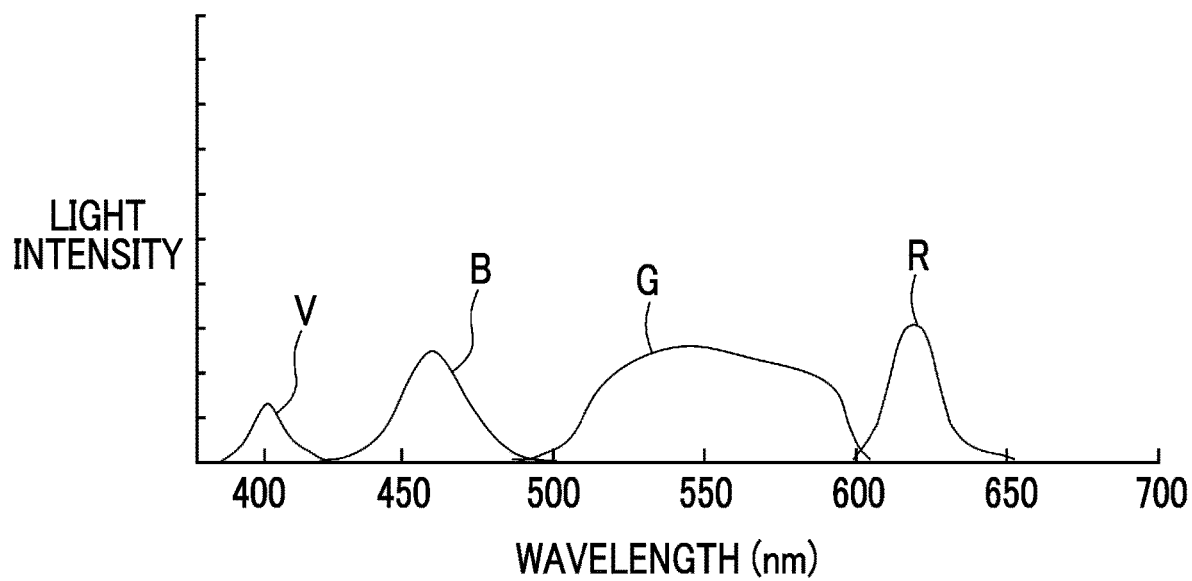
FIG. 3 is a graph showing the emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source control unit 21 performs control to turn on the V-LED 20a, the B-LED 20b, the G-LED 20c, and the R-LED 20d in all observation modes. Further, the light source control unit 21 controls the respective LEDs 20a to 20d so that normal light of which the light intensity ratios of violet light V, blue light B, green light G, and red light R are Vc:Bc:Gc:Rc is emitted in the normal observation mode. In this specification, a light emission ratio means the light intensity ratio of each semiconductor light source and includes a case where the light intensity ratio is 0 (zero). Accordingly, the light emission ratio includes a case where any one or two of the respective semiconductor light sources are not turned on. For example, even in a case where only one semiconductor light source is turned on and the other three semiconductor light sources are not turned on as in a case where the light intensity ratios of violet light V, blue light B, green light G, and red light R are 1:0:0:0, it is considered that the light source unit has a light emission ratio.

Figure 4:
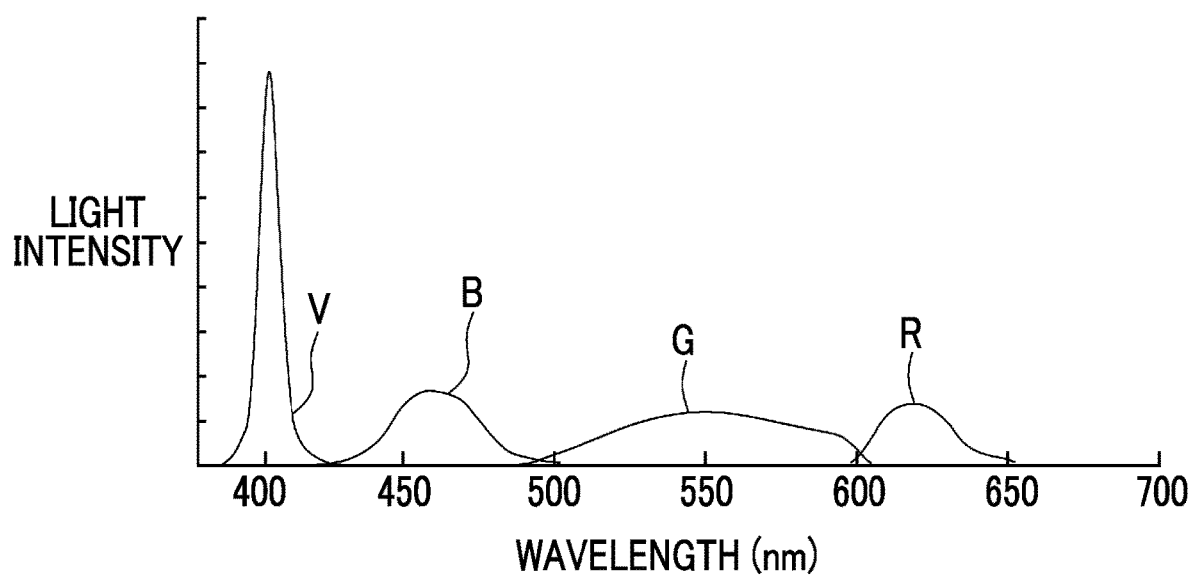
FIG. 4 is a graph showing the emission spectrum of first illumination light that includes violet light V, blue light B, green light G, and red light R.

Furthermore, the light source control unit 21 performs control to emit first illumination light of which the light intensity ratios of violet light V, blue light B, green light G, and red light R are Vs1:Bs1:Gs1:Rs1, to acquire the first image that is emphasized superficial blood vessels, in a case where a mode is set to the multi-observation mode. To emphasize superficial blood vessels, it is preferable that the first illumination light has a peak in the range of 400 nm to 440 nm. For this purpose, the light intensity ratios Vs1:Bs1:Gs1:Rs1 of the first illumination light are set so that the light intensity of violet light V is higher than the light intensity of each of blue light B, green light G, and red light R as shown in FIG. 4 (Vs1>Bs1, Gs1, and Rs1). Further, since the first illumination light includes a first red-light wavelength range like red light R, the first illumination light can accurately reproduce the color of a mucous membrane. Furthermore, since the first illumination light includes a first blue-light wavelength range and a first green-light wavelength range like violet light V, blue light B, and green light G, the first illumination light can also emphasize various structures, such as glandular structures and unevenness, in addition to the above-mentioned superficial blood vessels.

Moreover, the light source control unit 21 performs control to emit second illumination light of which the light intensity ratios of violet light V, blue light B, green light G, and red light R are Vs2:Bs2:Gs2:Rs2 as a light emission ratio in a second observation mode, to emphasize deep blood vessels and to acquire the second image in the multi-observation mode. To emphasize deep blood vessels, it is preferable that the intensity ratio of the second illumination light is higher than that of the first illumination light in at least one of wavelengths of 460 nm, 540 nm, or 630 nm.

Figure 5:
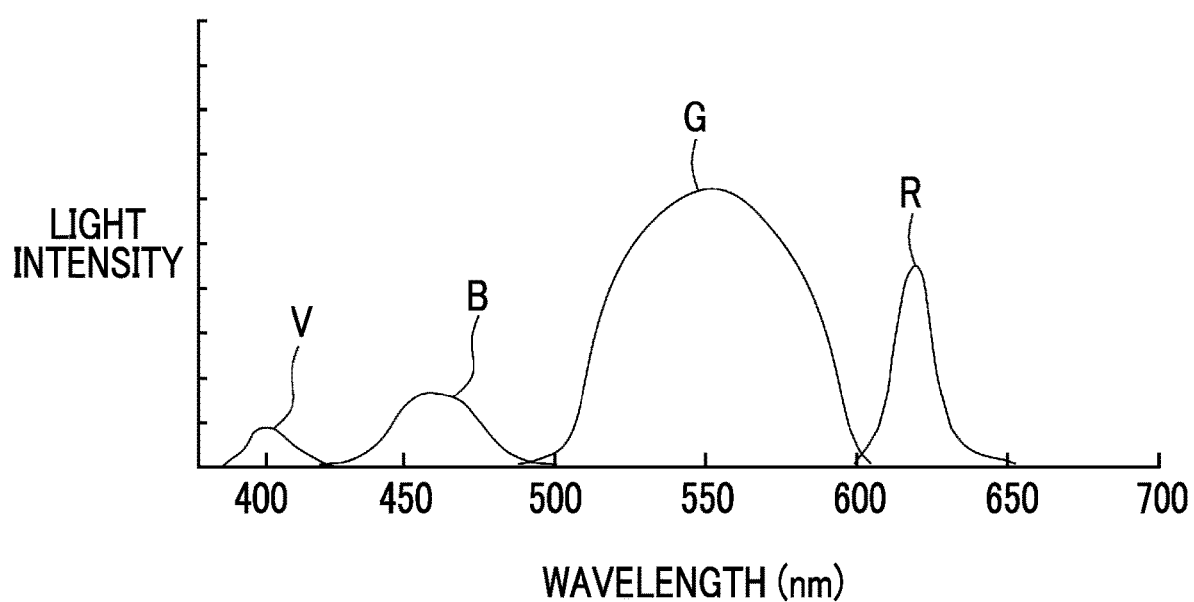
FIG. 5 is a graph showing the emission spectrum of second illumination light that includes violet light V, blue light B, green light G, and red light R.

For this purpose, the light intensity ratios Vs2:Bs2:Gs2:Rs2 of the second illumination light are set so that the amount of green light G or red light R of the second illumination light is larger than the amounts of blue light B, green light G, and red light R of the first illumination light as shown in FIG. 5. Further, since the second illumination light includes a second red-light wavelength range like red light R, the second illumination light can accurately reproduce the color of a mucous membrane. Furthermore, since the second illumination light includes a second blue-light wavelength range and a second green-light wavelength range like violet light V, blue light B, and green light G, the second illumination light can also emphasize various structures, such as unevenness, in addition to the above-mentioned deep blood vessels.

Figure 6:
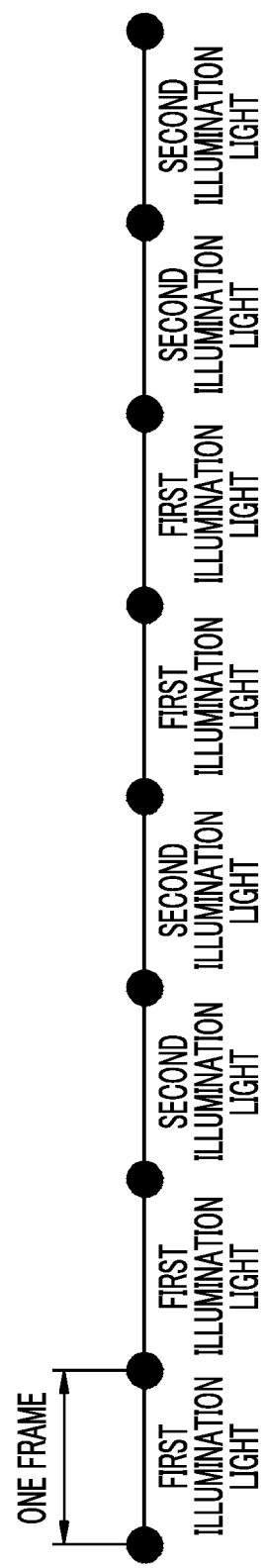
FIG. 6 is a diagram showing the light emission period of the first illumination light and the light emission period of the second illumination light.

In a case where a mode is set to the multi-observation mode, the light source control unit 21 performs control to emit each of the first illumination light and the second illumination light for a light emission period of two or more frames and to automatically switch and emit the first illumination light and the second illumination light. For example, in a case where the light emission period of the first illumination light is set to two frames and the light emission period of the second illumination light is also set to two frames, the second illumination light also continues to be emitted for two frames after the first illumination light continues to be emitted for two frames as shown in FIG. 6. Here, each of the light emission period of the first illumination light and the light emission period of the second illumination light is set to a period of at least two or more frames. The reason why each light emission period is set to a period of two or more frames as described above is that the illumination light of the light source device 14 is immediately switched but at least two or more frames are required to switch the image processing of the processor device 16. In addition, since there is a case where flicker occurs due to the switching of illumination light, each light emission period is set to a period of two or more frames to reduce a burden on an operator caused by flicker. "Frame" means a unit used to control an image pickup sensor 48 that picks up the image of an object to be observed. For example, "one frame" means a period including at least an exposure period where the image pickup sensor 48 is exposed to light emitted from an object to be observed and a read-out period where image signals are read out. In this embodiment, a light emission period is determined so as to correspond to "frame" that is a unit of image pickup.

Figure 7:
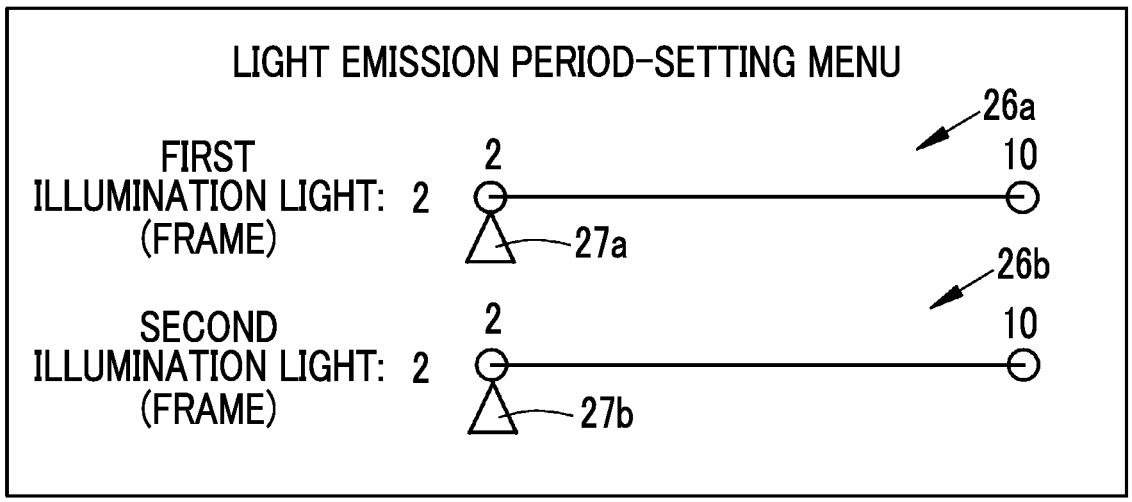
FIG. 7 is a diagram showing a light emission period-setting menu.

The light emission period of the first illumination light and the light emission period of the second illumination light can be appropriately changed by a light emission period-setting unit 24 (see FIG. 2) that is connected to the light source control unit 21. In a case where an operation for changing a light emission period is received by the operation of the keyboard 19, the light emission period-setting unit 24 displays a light emission period-setting menu shown in FIG. 7 on the monitor 18. The light emission period of the first illumination light can be changed between, for example, two frames and ten frames. Each light emission period is assigned to a slide bar 26a.

In a case where the light emission period of the first illumination light is to be changed, a user operates the keyboard 19 to position a slider 27a at a position on the slide bar 26a that represents a light emission period to which the user wants to change a light emission period. Accordingly, the light emission period of the first illumination light is changed. Even in the case of the light emission period of the second illumination light, a user operates the keyboard 19 to position a slider 27b at a position on a slide bar 26b (to which a light emission period in the range of, for example, two frames to ten frames is assigned) that represents a light emission period to which the user wants to change a light emission period. Accordingly, the light emission period of the second illumination light is changed. In a case where there are two kinds of illumination light, the first illumination light and the second illumination light are emitted alternately with regard to the order of emission of the plurality of kinds of illumination light. In a case where the plurality of kinds of illumination light are three or more kinds of illumination light, the order of emission of the respective kinds of illumination light can be randomly set.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 µm, a cladding diameter of 125 µm, and a protective layer forming a covering is in the range of φ 0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor that is used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source control unit 21 causes blue light B, green light G, and red light R to be emitted in a time-sharing manner, demosaicing needs to be added to the processing of image pickup signals.

The image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 corresponds to a medical image processing device that processes medical images, such as images obtained by the endoscope 12. The processor device 16 comprises an image acquisition unit 53, a digital signal processor (DSP) 56, a noise removing unit 58, a central control unit 66, an image processing unit 60, and a display control unit 62. Digital color image signals output from the endoscope 12 are input to the image acquisition unit 53. The color image signals are RGB image signals formed of R-image signals that are output from the R-pixels of the image pickup sensor 48, G-image signals that are output from the G-pixels of the image pickup sensor 48, and B-image signals that are output from the B-pixels of the image pickup sensor 48.

The DSP 56 performs various kinds of signal processing, such as defect correction processing, offset processing, gain correction processing, linear matrix processing, gamma conversion processing, and demosaicing processing, on the received image signals. Signals of defective pixels of the image pickup sensor 48 are corrected in the defect correction processing. Dark current components are removed from the RGB image signals having been subjected to the defect correction processing in the offset processing, so that an accurate zero level is set. The RGB image signals having been subjected to the offset processing are multiplied by a specific gain in the gain correction processing, so that signal levels are adjusted. The linear matrix processing for improving color reproducibility is performed on the RGB image signals having been subjected to the gain correction processing. After that, brightness or a saturation is adjusted by the gamma conversion processing. The demosaicing processing (also referred to as equalization processing or demosaicing) is performed on the RGB image signals having been subjected to the linear matrix processing, so that signals of colors deficient in each pixel are generated by interpolation. All the pixels are made to have the signals of the respective colors of R, G, and B by this demosaicing processing.

The noise removing unit 58 performs noise removal processing (for example, a moving-average method, a median filtering method, or the like) on the RGB image signals, which have been subjected to gamma correction and the like by the DSP 56, to remove noise from the RGB image signals. The RGB image signals from which noise has been removed are transmitted to the image processing unit 60.

The image processing unit 60 performs various kinds of image processing on the RGB image signals. The RGB image signals having been subjected to the image processing are sent to the display control unit 62. The image processing, which is performed by the image processing unit 60, varies for each observation mode. Image processing for a normal observation mode corresponding to the normal observation mode is performed on the RGB image signals in the normal observation mode, and image processing for a multi-observation mode corresponding to the multi-observation mode is performed on the RGB image signals in the multi-observation mode. Further, processing for storing the first and second images as a set in a case where a static-image-acquisition instruction is given and storing the first and second images as static images for storage in a case where a specific condition is satisfied with regard to the shake amount is performed in the multi-observation mode. The details of the image processing unit 60 and processing to be performed at the time of a static-image-acquisition instruction in the multi-observation mode will be described later.

The display control unit 62 performs control to display an image, which corresponds to the each observation mode, on the monitor 18 on the basis of the RGB image signals having been subjected to the image processing. In the normal observation mode, the display control unit 62 performs control to display a normal image, which is obtained on the basis of the emission of normal light, on the monitor 18. In the multi-observation mode, the display control unit 62 performs control to display the first image, which is obtained on the basis of the emission of the first illumination light, and the second image, which is obtained on the basis of the emission of the second illumination light, on the monitor 18 while switching the first and second images according to a display condition that includes a specific display order or a specific display time.

Figure 8:
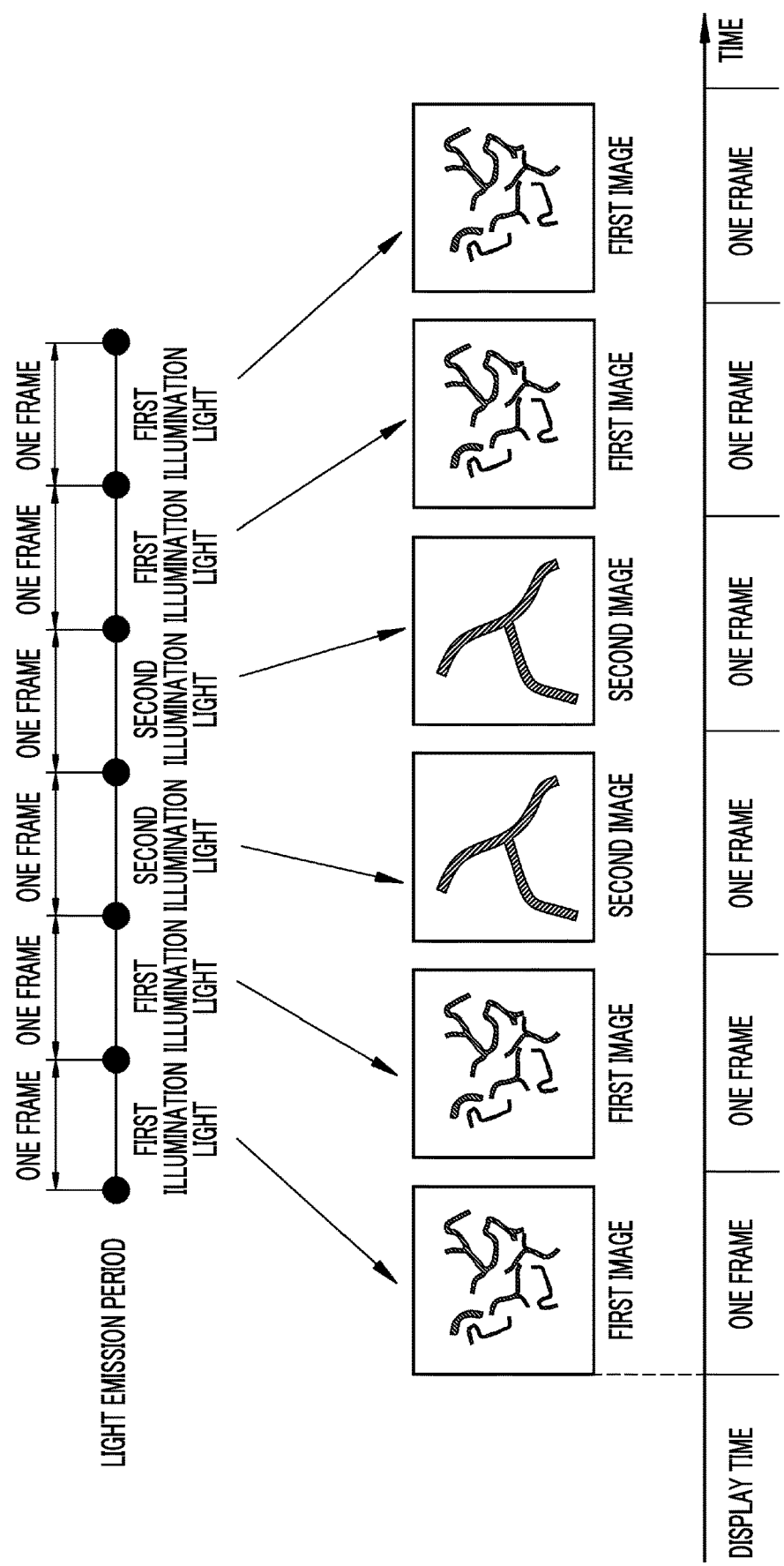
FIG. 8 is a diagram showing the switching display of a first image and a second image.

For example, in a case where the specific display order corresponds to "first image→second image" and the display time of the first image is "two frames" and the display time of the second image is "two frames" with regard to the specific display time, the first and second images are displayed on the monitor 18 while being switched at an interval of two frames according to the first illumination light and the second illumination light that are emitted at an interval of two frames as shown in FIG. 8. The first image is displayed so that relatively thin superficial blood vessels are emphasized, and the second image is displayed so that relatively thick deep blood vessels are emphasized.

The central control unit 66 controls the respective parts of the processor device 16. Further, the central control unit 66 receives information from the endoscope 12 and the light source device 14, and performs the control of the respective parts of the processor device 16 and the control of the endoscope 12 or the light source device 14 on the basis of the received information. Furthermore, the central control unit 66 also receives information, such as an instruction input from the keyboard 19.

Figure 9:
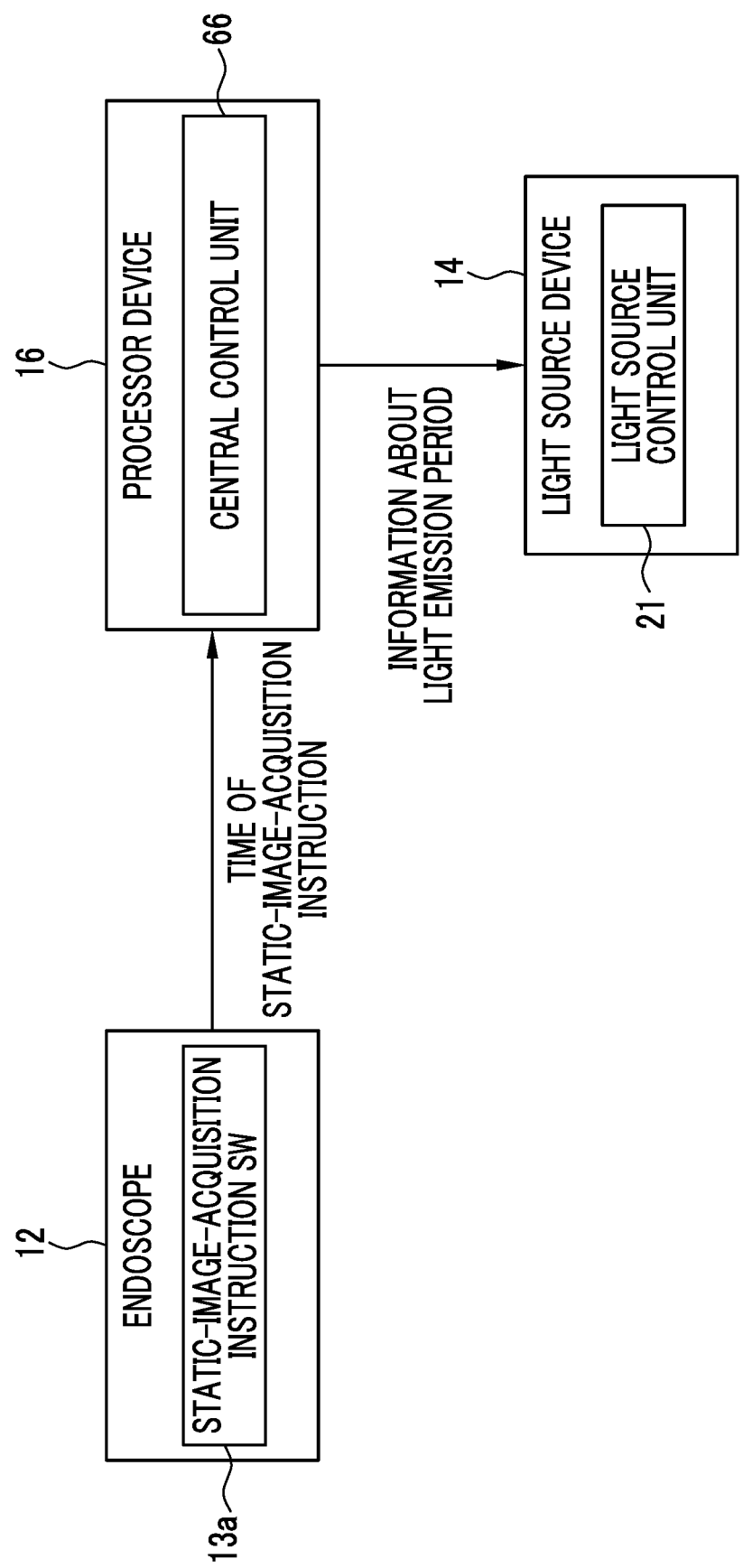
FIG. 9 is a block diagram showing the flow of information in a case where a static-image-acquisition instruction is given.

For example, in a case where the static-image-acquisition instruction SW 13a is operated in the endoscope 12 as shown in FIG. 9, information about a static-image-acquisition instruction is transmitted to the central control unit 66. The central control unit 66 sends the information about the static-image-acquisition instruction to the image processing unit 60. The storage of the static images is controlled in the image processing unit 60 using the information about the static-image-acquisition instruction. In this embodiment, the information about the static-image-acquisition instruction is a time when the static-image-acquisition instruction is given. Further, information about the light emission periods of the first illumination light and the second illumination light set by the operation of the keyboard 19 is input to the processor device 16, and is sent to the light source device 14 through the processor device 16. The light source control unit of the light source device 14 controls the light sources on the basis of the information about the light emission periods sent from the processor device 16.

Figure 10:
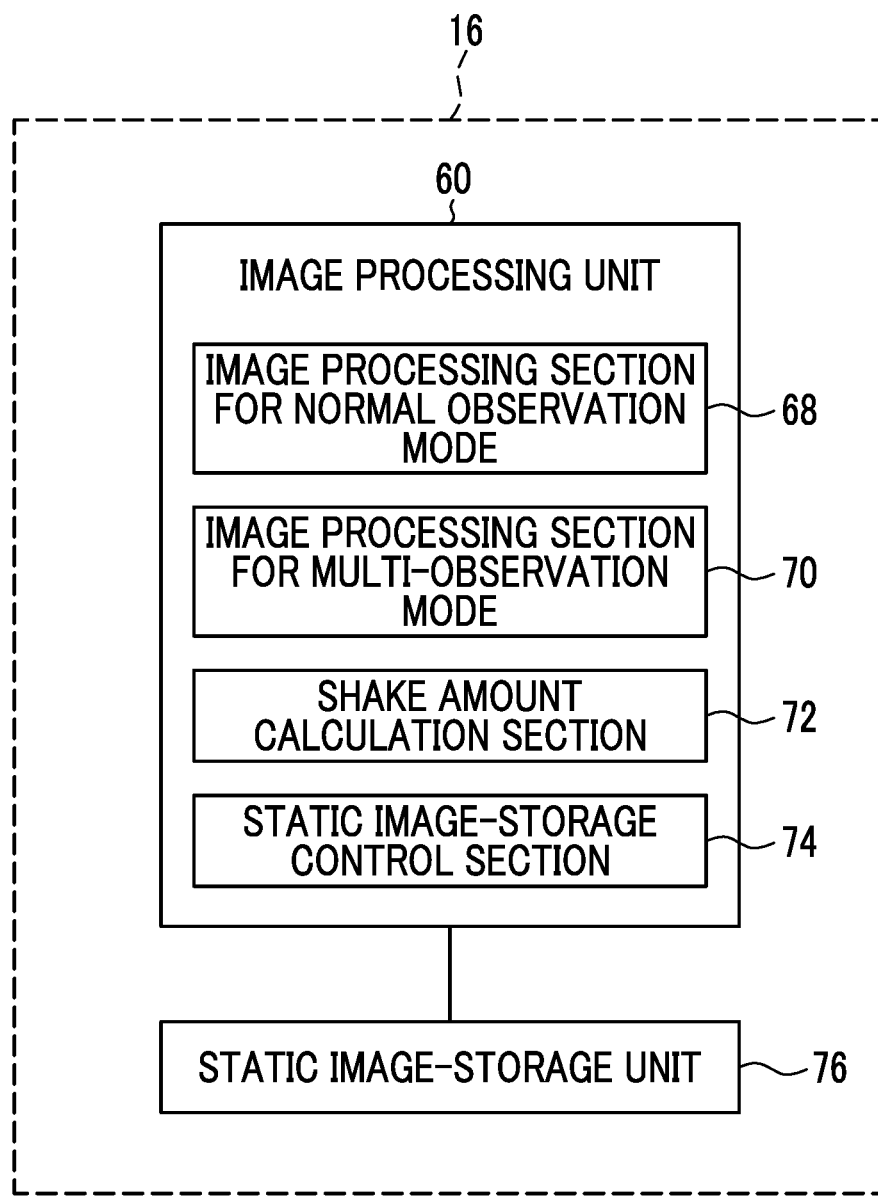
FIG. 10 is a block diagram showing an image processing unit and a static image-storage unit.

The details of the image processing unit 60 and processing to be performed at the time of the static-image-acquisition instruction in the multi-observation mode will be described below. As shown in FIG. 10, the image processing unit 60 includes a shake amount calculation section 72 and a static image-storage control section 74 in addition to an image processing section 68 for a normal observation mode and an image processing section 70 for a multi-observation mode. The image processing section 68 for a normal observation mode performs image processing for a normal observation mode on the RGB image signals. This image processing for a normal observation mode is performed, so that a normal image is obtained. The image processing section 70 for a multi-observation mode performs image processing for a multi-observation mode on the RGB image signals. The image processing for a multi-observation mode includes image processing for first illumination light that is performed on the RGB image signals obtained at the time of emission of the first illumination light, and image processing for second illumination light that is performed on the RGB image signals obtained at the time of emission of the second illumination light. The image processing for first illumination light is performed, so that a first image is obtained. The image processing for second illumination light is performed, so that a second image is obtained. To reduce the burden of the processing performed by the image processing unit 60, it is preferable that the same kind of processing, such as color emphasis processing and structure emphasis processing, is performed as the image processing for a normal observation mode, the image processing for first illumination light, and the image processing for second illumination light, and it is preferable that only parameters used in these kinds of processing (parameters for color emphasis processing and parameters for structure emphasis processing) are set to be different.

The shake amount calculation section 72 calculates a shake amount by performing shake amount-calculation processing according to the signal of the static-image-acquisition instruction sent from the central control unit 66. Further, the static image-storage control section 74 performs control to store images, of which the shake amounts satisfy the specific condition, in a static image-storage unit 76 as static images for storage. In the various kinds of image processing, image processing performed under the same condition regardless of an observation mode can also be performed in addition to image processing that is performed under a condition varying for each observation mode.

Figure 11:
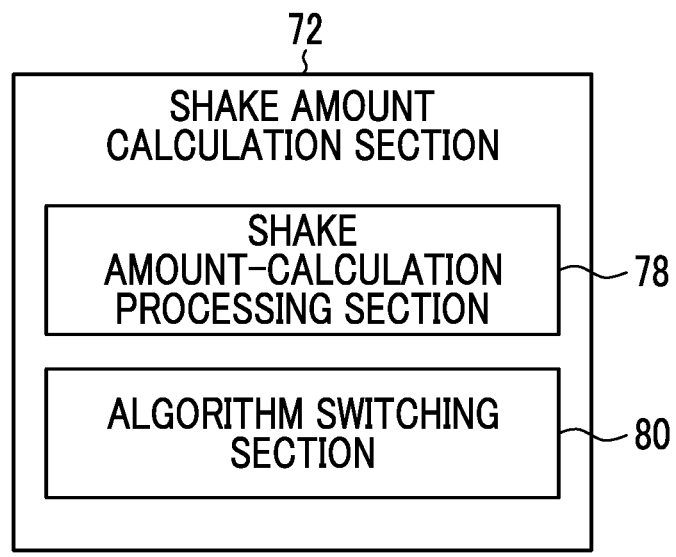
FIG. 11 is a block diagram of a shake amount calculation section.

As shown in FIG. 11, the shake amount calculation section 72 includes a shake amount-calculation processing section 78 and an algorithm switching section 80. In a case where a static-image-acquisition instruction is given, the shake amount-calculation processing section 78 performs shake amount-calculation processing for calculating the shake amounts of a plurality of images that are acquired in a specific static-image-acquisition instruction period Tp including the timing of the static-image-acquisition instruction. In this embodiment, the shake amount-calculation processing section 78 performs the shake amount-calculation processing on all the images obtained in the specific static-image-acquisition instruction period Tp.

Figure 12:
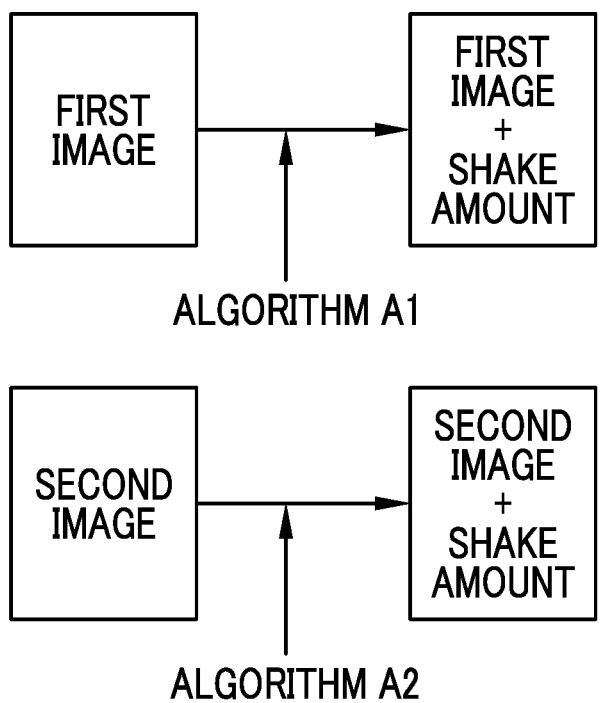
FIG. 12 is a diagram showing a relationship between an image and an algorithm for calculating a shake amount.

The static-image-acquisition instruction period Tp (see FIG. 13) can be randomly set. However, for example, in this embodiment, the static-image-acquisition instruction period Tp is set to a period in which at least four image sets, each of which corresponds to four frames and is formed of first images for two frames and second images for two frames, that is, images for sixteen frames can be acquired from the timing of the static-image-acquisition instruction. As shown in FIG. 12, shake amount-calculation processing is performed on the first image obtained using the first illumination light by an algorithm A1 that is first shake amount-calculation processing, and shake amount-calculation processing is performed on the second image obtained using the second illumination light by an algorithm A2 that is second shake amount-calculation processing. Superficial blood vessels and the like, which are objects to be emphasized by light having a short wavelength, correspond to an important structure in an image in a first observation mode using the first illumination light. Accordingly, the algorithm A1 is formed of a shake amount calculation algorithm for calculating a shake amount using B-image signals (blue spectral image), which include much information about violet light V or blue light B serving as light having a short wavelength, of the first image. Further, deep blood vessels and the like, which are objects to be emphasized by light having a medium wavelength, correspond to an important structure in an image in a second observation mode using the second illumination light. Accordingly, the algorithm A2 is formed of a shake amount calculation algorithm for calculating a shake amount using G-image signals (green spectral image), which include much information about green light G serving as light having a medium wavelength, of the second image. Therefore, since the shake amount of a spectral image of a color where the important structure is emphasized in each image is calculated, a shake amount can be accurately calculated.

The first shake amount-calculation processing and the second shake amount-calculation processing are formed of the same algorithm except that spectral images to be used are different from each other. It is preferable that a shake amount is a vector quantity having the direction and magnitude of the shake of an image. The calculated shake amount is associated with images, and static images to be stored as static images for storage are selected on the basis of the shake amount.

As a method of calculating a shake amount, there are mainly a method based on image analysis and a method based on the image pickup sensor 48. However, the method based on image analysis is employed in this embodiment. As the method based on image analysis, there is a method including a step of estimating a point spread function (PSF) for each of a plurality of regions of an image and a step of estimating the direction and magnitude of shake from the point spread function with high accuracy (see JP5499050B). Further, a shake that is represented in a frequency space as a power spectrum convoluted with a sinc function in a shaken image generated due to the linear operation of the endoscope 12 is known among shakes. In a situation where such a shaken image is often generated, it is preferable that image signals are converted into the image of a frequency region and a shake amount is detected on the basis of the degree of the influence of a sinc function generated in a shake direction in the image of the frequency region (see JP2009-230598A). Furthermore, there is a method including a step of detecting a movement vector from image signals and a step of detecting the shake amount of an image on the basis of the movement vector (see JP1991-016470A (JP-H03-016470A)). Moreover, a method including a step of calculating a contrast and a step of detecting an image having a large contrast as an image of which the shake amount is small is also preferably used.

The algorithm switching section 80 switches the algorithm for the shake amount-calculation processing for each observation mode in a case where an image is acquired. That is, different shake amount-calculation processing is performed depending on an observation mode in a case where an image, which is an object of which the shake amount is to be calculated, is acquired.

Since information about the light emission period of the light emission period-setting unit 22 and a static-image-acquisition instruction are sent to the algorithm switching section 80 from the central control unit 66, information about the time of the static-image-acquisition instruction is also sent to the algorithm switching section 80. Accordingly, in a case where the static-image-acquisition instruction is given, the algorithm switching section 80 can determine which observation mode a plurality of images acquired in the specific static-image-acquisition instruction period Tp including the time (timing) of the static-image-acquisition instruction are based on, on the basis of information about the time of the static-image-acquisition instruction and the light emission period. In a case where the acquired image itself has information about the time when the image is acquired as additional information, the algorithm switching section 80 can also recognize the time when the image is acquired from each image.

Since the algorithm switching section 80 is configured as described above, the algorithm switching section 80 can correctly switch the algorithm for the shake amount-calculation processing for each observation mode where each image is acquired. That is, in the static-image-acquisition instruction period Tp, the algorithm switching section 80 performs processing for switching the shake amount-calculation processing to the algorithm A1 in a case where the first image is to be acquired and switching the shake amount-calculation processing to the algorithm A2 in a case where the second image is to be acquired. Then, in a case a shake amount is to be calculated, the processor device 16 including the shake amount calculation section 72 does not excessively control the endoscope 12 and the light source device 14, the light source device 14 can perform processing using the parameters of the light source device 14 itself, and the shake amount calculation section 72 can also perform processing using the parameters of the shake amount calculation section 72 itself. Accordingly, a shake amount can be calculated while a load on the system is reduced.

In this embodiment, the static image-storage control section 74 calculates the shake amount of every image of the image sets obtained in the specific static-image-acquisition instruction period Tp, and sums up the calculated shake amounts of the images to calculate the sums of the calculated shake amounts as representative shake amounts. Then, the static image-storage control section 74 selects an image set, which has the smallest representative shake amount, among the image sets obtained in the specific static-image-acquisition instruction period as an image set satisfying the specific condition, and stores the selected image set in the static image-storage unit 76 as static images for storage. Further, in a case where the static image-storage control section 74 stores the static images for storage in the static image-storage unit 76, the static image-storage control section 74 associates the static images for storage with a display condition including a display order or a display time and stores the static images for storage in the static image-storage unit 76.

Accordingly, in a playback mode to be performed after endoscopic diagnosis, the static images for storage stored in the static image-storage unit 76 can be displayed according to the same display condition as a display condition during diagnosis. For example, in a case where a display condition is a condition where the first and second images are displayed while being switched at an interval of two frames, the first and second images of the static images for storage can also be displayed while being switched at an interval of two frames. The switching of a mode to the playback mode can be performed by the keyboard 19. Further, the static images for storage stored in the static image-storage unit 76 and a display condition may be transmitted to a medical computer separate from the endoscope system 10, and the static images for storage may be played back in the medical computer according to the display condition. In this case, an endoscopic image-playback program for playing back the static images for storage is installed on the medical computer. The specific condition can be randomly set. For example, a threshold value may be set in advance, and all images of which the shake amounts are smaller than the threshold value may be stored.

Figure 13:
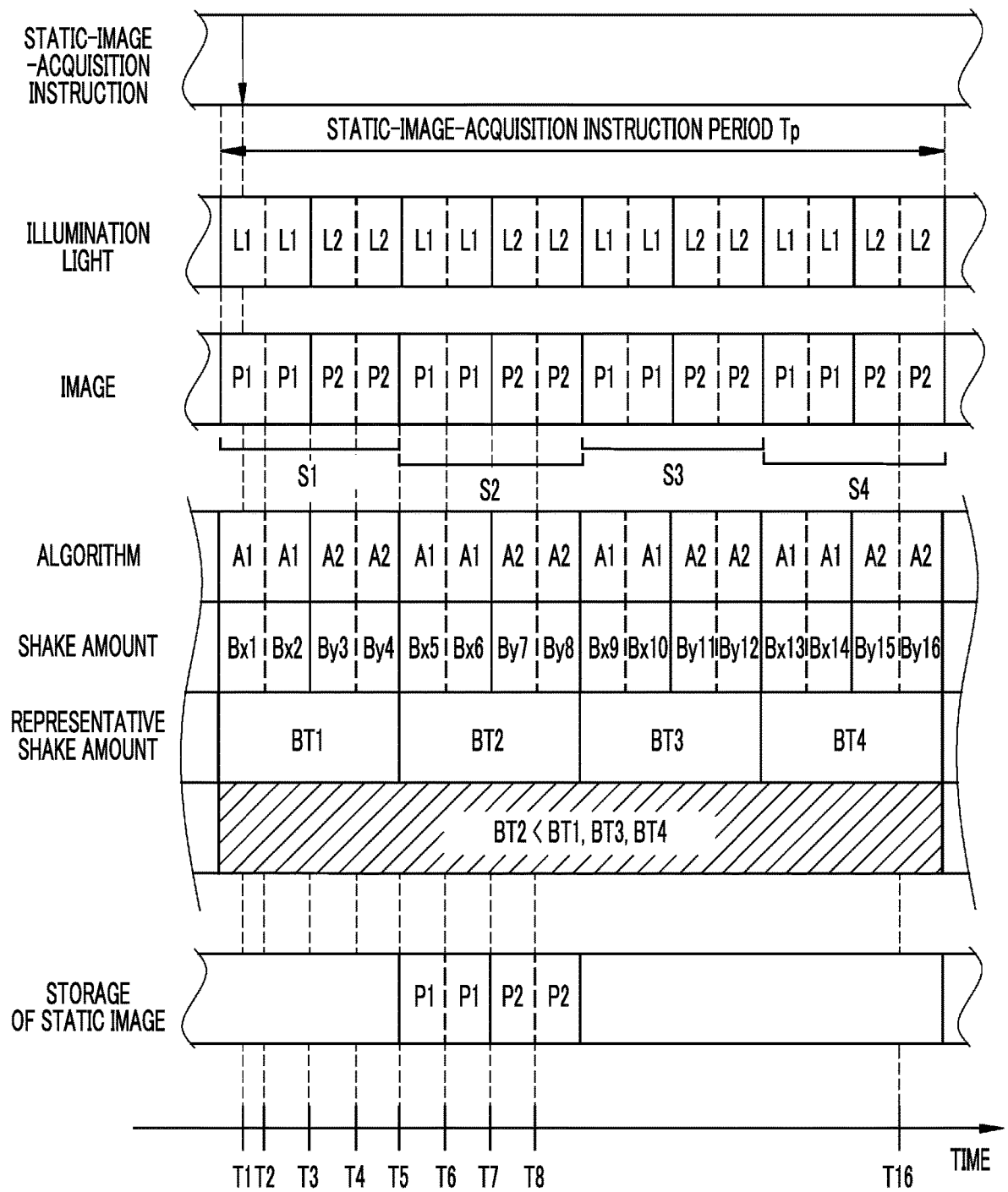

The control of the storage of the static images performed by the static image-storage control section 74 will be described with reference to FIG. 13. In a case where a static-image-acquisition instruction is given at a timing T1, a period Tp from the timing T1 to a timing Tn (n is a natural number of 2 or more) is set as the specific static-image-acquisition instruction period Tp. The specific static-image-acquisition instruction period Tp is a period in which four image sets (one image set is formed of images for four frames), that is, images for sixteen frames can be acquired as described above. Accordingly, the specific static-image-acquisition instruction period Tp is a period from the timing T1 to a timing T16.

Even in the specific static-image-acquisition instruction period Tp, first illumination light L1 and second illumination light L2 are emitted while being switched at an interval of two frames. Further, first images P1 for two frames are obtained according to the emission of the first illumination light for two frames, and second images P2 for two frames are obtained according to the emission of the second illumination light for two frame that is to be emitted after the first illumination light. The acquisition of the first images for two frames and the acquisition of the second images for two frames are alternately performed. Accordingly, an image set S1, which is formed of first images P1 obtained at the timings T1 and T2 and second images P2 obtained at the timings T3 and T4, is obtained in a period from the timing T1 to the timing T4. Likewise, an image set S2, which is formed of first images P1 obtained at the timings T5 and T6 and the second images P2 obtained at the timings T7 and T8, is obtained in a period from the timing T5 to the timing T8. Furthermore, an image set S3, which is formed of first images P1 obtained at the timings T9 and T10 and the second images P2 obtained at the timings T11 and T12, is obtained. Moreover, an image set S4, which is formed of first images P1 obtained at the timings T13 and T14 and the second images P2 obtained at the timings T15 and T16, is obtained.

Then, shake amount-calculation processing is performed on every image of each image set. In this shake amount-calculation processing, the algorithm A1 is applied to the first image and the algorithm A2 is applied to the second image. The algorithm A1 is applied to the first images P1 obtained at the timings T1 and T2 in the case of the image set S1, so that shake amounts Bx1 and Bx2 at the timings T1 and T2 are calculated. On the other hand, the algorithm A2 is applied to the second images P2 obtained at the timings T3 and T4, so that shake amounts By3 and By4 at the timings T3 and T4 are calculated. Likewise, shake amount-calculation processing is performed on every image of the image set S2, so that shake amounts Bx5, Bx6, By7, and By8 are calculated. Further, shake amount-calculation processing is performed on the images of the image set S3, so that shake amounts Bx9, Bx10, By11, and By12 are calculated. Furthermore, shake amount-calculation processing is performed on the images of the image set S4, so that shake amounts Bx13, Bx14, By15, and By16 are calculated.

Next, the static image-storage control section 74 sums up the shake amounts, which are calculated from the every image set, to calculate representative shake amounts. In the case of the image set S1, the static image-storage control section 74 sums up the shake amounts Bx1, Bx2, By3, and By4 to obtain a representative shake amount BT1. Likewise, in the case of the image set S2, the static image-storage control section 74 sums up the shake amounts Bx5, Bx6, By7, and By8 to obtain a representative shake amount BT2. Further, in the case of the image set S3, the static image-storage control section 74 sums up the shake amounts Bx9, Bx10, By11, and By12 to obtain a representative shake amount BT3. Furthermore, in the case of the image set S4, the static image-storage control section 74 sums up the shake amounts Bx13, Bx14, By15, and By16 to obtain a representative shake amount BT4.

Then, the static image-storage control section 74 selects an image set, which has the smallest representative shake amount, among the image sets S1 to S4 as static images for storage. For example, in a case where the representative shake amount BT2 is smallest (BT2<BT1, BT3, and BT4), the image set S2 formed of the first images obtained at the timings T5 and T6 and the second images obtained at the timings T7 and T8 is selected as the static images for storage.

In this embodiment, the static image-storage control section 74 calculates a shake amount (a representative shake amount) as a unit of the image set and selects an image set, which has the smallest representative shake amount, as the static images for storage. However, the invention is not limited to this method. For example, among the plurality of images obtained in the specific static-image-acquisition instruction period Tp, a first image having the smallest shake amount with regard to the first images and a second image having the smallest shake amount with regard to the second images may be selected as the static images for storage.

Second Embodiment

In the first embodiment, the calculation of shake amounts and the storage of static images for storage are performed for images that are obtained after a static-image-acquisition instruction is given. However, in a second embodiment, the calculation of shake amounts and the storage of static images for storage are performed for temporarily stored videos that are the videos of a plurality of images obtained in a specific period in advance. That is, in the first embodiment, images obtained after a static-image-acquisition instruction is given are used as an object for the calculation of shake amounts and the storage of static images for storage. However, in the second embodiment, images obtained before a static-image-acquisition instruction is given are used as an object for the calculation of shake amounts and the storage of static images for storage. Since the second embodiment is the same as the first embodiment except for the above-mentioned point, devices and the like, which are denoted in FIGS. 14 and 15 by the same reference numerals as those of FIGS. 1 to 13, are the same as those of the first embodiment. Accordingly, the description of the devices and the like will be omitted.

Figure 14:
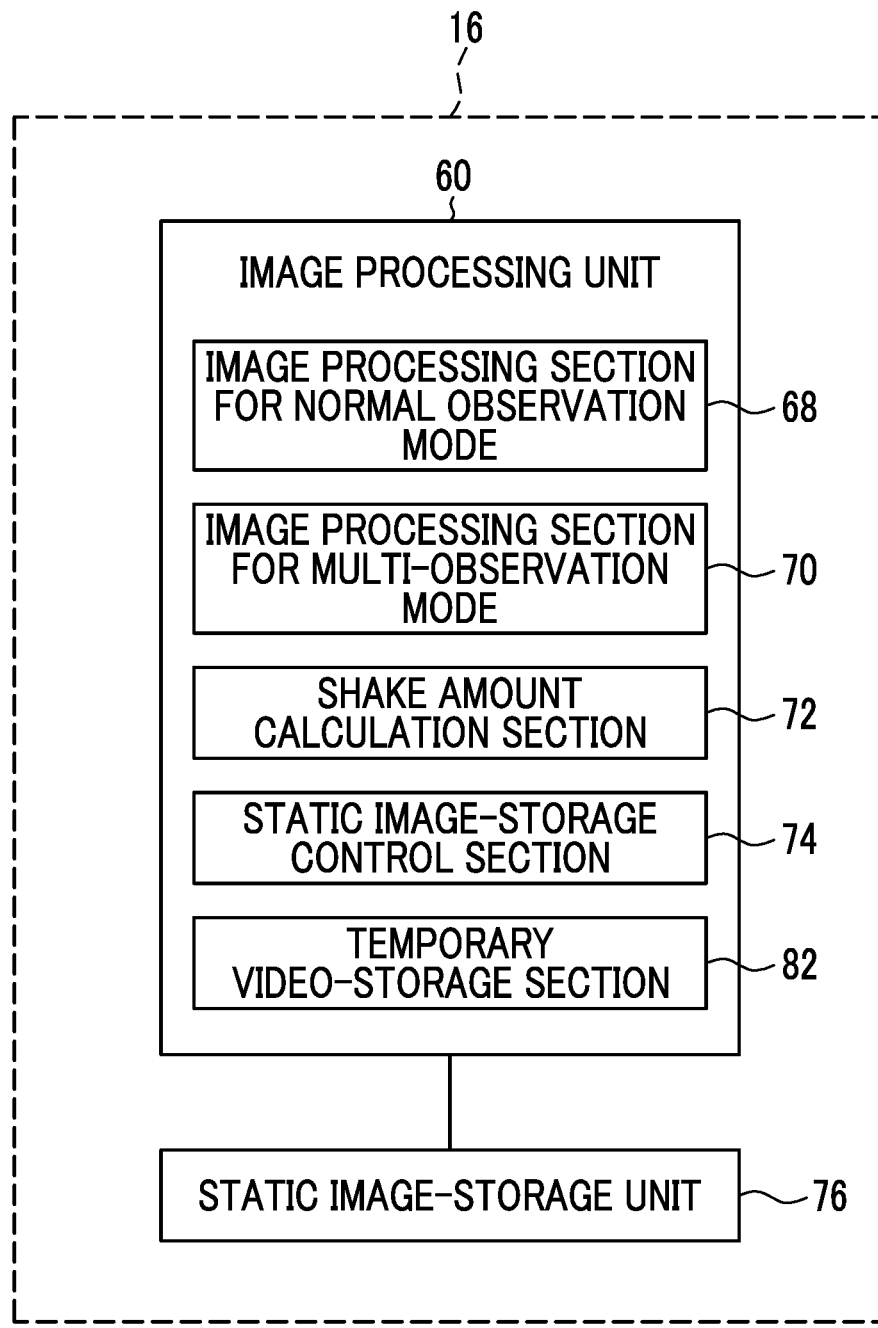
FIG. 14 is a block diagram showing the image processing unit.

As shown in FIG. 14, an image processing unit 60 of this embodiment includes a temporary video-storage section 82 in addition to the image processing section 68 for a normal observation mode, the image processing section 70 for a multi-observation mode, the shake amount calculation section 72, and the static image-storage control section 74. The temporary video-storage section 82 always stores the videos of images obtained in a specific period, which dates back from the current point of time, according to settings, and automatically updates the stored videos. Any method can also be employed as a method of storing and updating a video, but a method including storing a predetermined number of videos of a specific period (temporary video storage period Tq) at a specific time interval and deleting the oldest videos, which are acquired at the earliest time, first in a case where new videos are stored is employed in this embodiment. Then, in a case where a static-image-acquisition instruction is given, one of the newest videos is selected from videos including the time thereof and a shake amount is calculated for each frame included in this video. Accordingly, in this embodiment, a period, which includes the latest time, of the temporary video storage period Tq including the time of the static-image-acquisition instruction is a static-image-acquisition instruction period.

Figure 15:
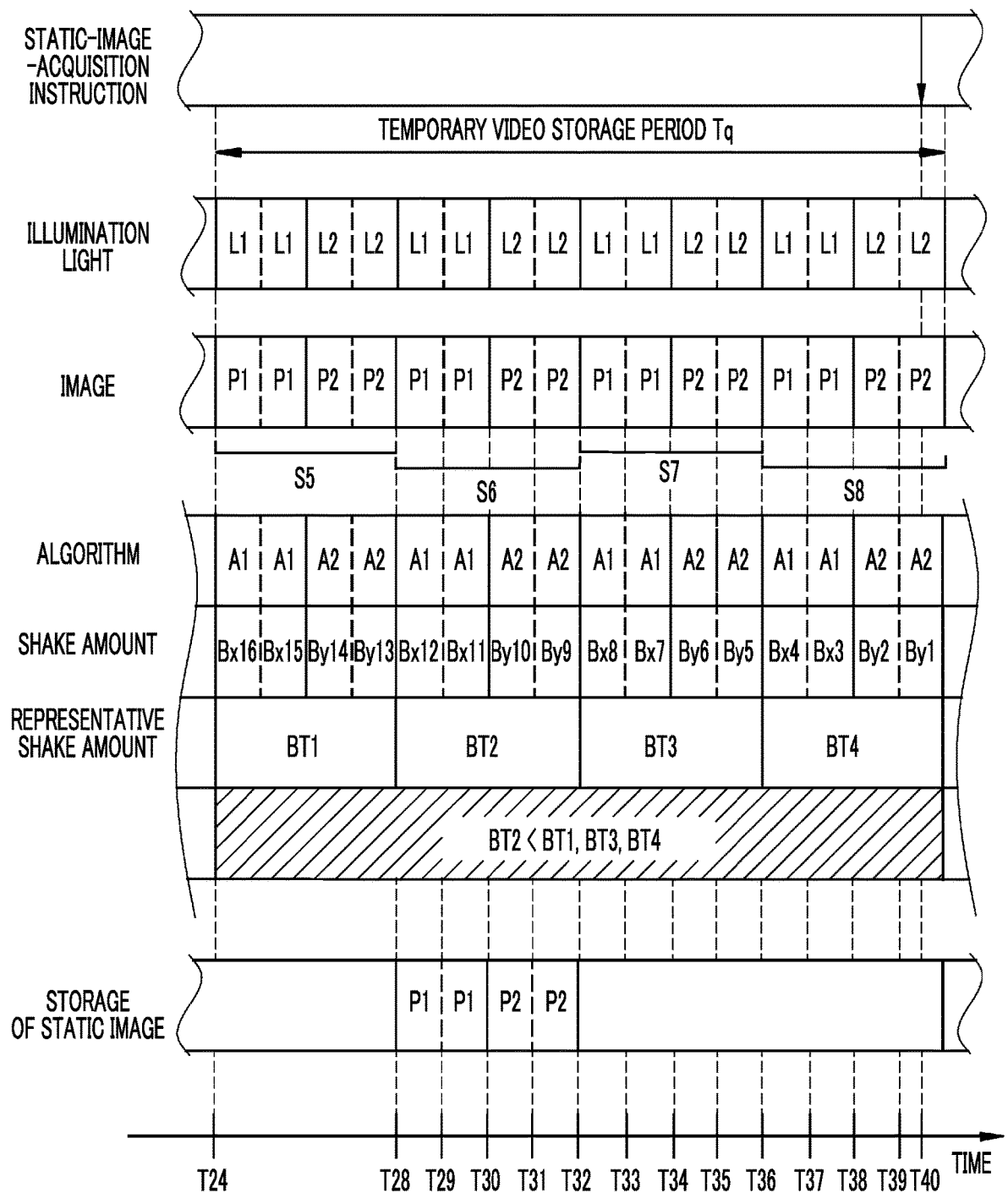

An object for the calculation of shake amounts in this embodiment will be described with reference to FIG. 15. In a case where a static-image-acquisition instruction is given at a timing T40, temporarily stored videos acquired in a temporary video storage period Tq including the timing T40 are set as an object for the calculation of shake amounts. The temporary video storage period Tq, which is a specific period, is a period which dates back from a timing T39 and in which four image sets (one image set is formed of images for four frames), that is, images for sixteen frames can be acquired. Accordingly, image acquisition timings included in the temporary video storage period Tq, which is a specific period, are timings T39 to T24.

As in the first embodiment, even in the temporary video storage period Tq that is a specific period, first illumination light L1 and second illumination light L2 are emitted while being switched at an interval of two frames. Further, first images P1 for two frames are obtained according to the emission of the first illumination light for two frames, and second images P2 for two frames are obtained according to the emission of the second illumination light for two frame that is to be emitted after the first illumination light. The acquisition of the first images for two frames and the acquisition of the second images for two frames are alternately performed. Accordingly, an image set S8, which is formed of second images P2 obtained at the timings T38 and T39 and first images P1 obtained at the timings T36 and T37, is obtained in a period from the timing T39 to the timing T36. Likewise, an image set S7, which is formed of second images P2 obtained at the timings T34 and T35 and first images P1 obtained at the timings T32 and T33, is obtained in a period from the timing T35 to the timing T32. Furthermore, an image set S6, which is formed of second images P2 obtained at the timings T30 and T31 and first images P1 obtained at the timings T28 and T29, is obtained. Moreover, an image set S5, which is formed of second images P2 obtained at the timings T26 and T27 and first images P1 obtained at the timings T24 and T25, is obtained.

Then, shake amount-calculation processing is performed on every image of each image set. In this shake amount-calculation processing, the algorithm A1 is applied to the first image and the algorithm A2 is applied to the second image. The algorithm A2 is applied to the second images P2 obtained at the timings T38 and T39 in the case of the image set S8, so that shake amounts By2 and By1 at the timings T38 and T39 are calculated. On the other hand, the algorithm A1 is applied to the first images P1 obtained at the timings T36 and T37, so that shake amounts Bx4 and Bx3 at the timings T36 and T37 are calculated. Likewise, shake amount-calculation processing is performed on every image of the image set S7, so that shake amounts By5, By6, Bx7, and Bx8 are calculated. Further, shake amount-calculation processing is performed on the images of the image set S6, so that shake amounts By9, By10, Bx11, and Bx12 are calculated. Furthermore, shake amount-calculation processing is performed on the images of the image set S5, so that shake amounts By13, By14, Bx15, and Bx16 are calculated.

Next, the static image-storage control section 74 sums up the shake amounts, which are calculated from the every image set, to calculate representative shake amounts. In the case of the image set S8, the static image-storage control section 74 sums up the shake amounts By1, By2, Bx3, and Bx4 to obtain a representative shake amount BT4. Likewise, in the case of the image set S7, the static image-storage control section 74 sums up the shake amounts By5, By6, Bx7, and Bx8 to obtain a representative shake amount BT3. Further, in the case of the image set S6, the static image-storage control section 74 sums up the shake amounts By9, By10, Bx11, and Bx12 to obtain a representative shake amount BT2. Furthermore, in the case of the image set S5, the static image-storage control section 74 sums up the shake amounts By13, By14, Bx15, and Bx16 to obtain a representative shake amount BT1.

Then, the static image-storage control section 74 selects an image set, which has the smallest representative shake amount, among the image sets S1 to S4 as static images for storage. For example, in a case where the representative shake amount BT2 is smallest (BT2<BT1, BT3, and BT4), the image set S6 formed of the second images obtained at the timings T30 and T31 and the first images obtained at the timings T28 and T29 is selected as the static images for storage.

In this embodiment, the static image-storage control section 74 calculates a shake amount (a representative shake amount) as a unit of the image set and selects an image set, which has the smallest representative shake amount, as the static images for storage. However, the invention is not limited to this method. For example, among the plurality of images obtained in the specific static-image-acquisition instruction period, a first image having the smallest shake amount with regard to the first images and a second image having the smallest shake amount with regard to the second images may be selected as the static images for storage.

Since this embodiment is adapted so that static images for storage are selected from images acquired in the past from a time when a static-image-acquisition instruction is given, a static image obtained at a point of time dating back from the current point of time can be acquired immediately after a user actually confirms an image. Accordingly, since a user does not need to return to an observation position to acquire a static image, this embodiment is efficient.

Third Embodiment

In the first and second embodiments, shake amounts start to be calculated after a static-image-acquisition instruction is given. However, the shake amounts of a plurality of images obtained in a specific period in advance are calculated in a third embodiment. Then, images having a small shake amount are stored in a temporary static-image-storage section 84 as static images for temporary storage, and static images for temporary storage, which are acquired in a static-image-acquisition instruction period Tr including the time of the static-image-acquisition instruction and the latest time, among the static images for temporary storage are sent to the static image-storage unit 76 as the static images for storage in a case where a static-image-acquisition instruction is given. That is, in the first and second embodiments, shake amounts are calculated after a static-image-acquisition instruction is given. However, in a third embodiment, shake amounts are calculated before a static-image-acquisition instruction is given, and images having a small shake amount are selected and stored. Since the third embodiment is the same as the first embodiment except for the above-mentioned point, devices and the like, which are denoted in FIGS. 16 and 17 by the same reference numerals as those of FIGS. 1 to 15, are the same as those of the first embodiment. Accordingly, the description of the devices and the like will be omitted.

Figure 16:
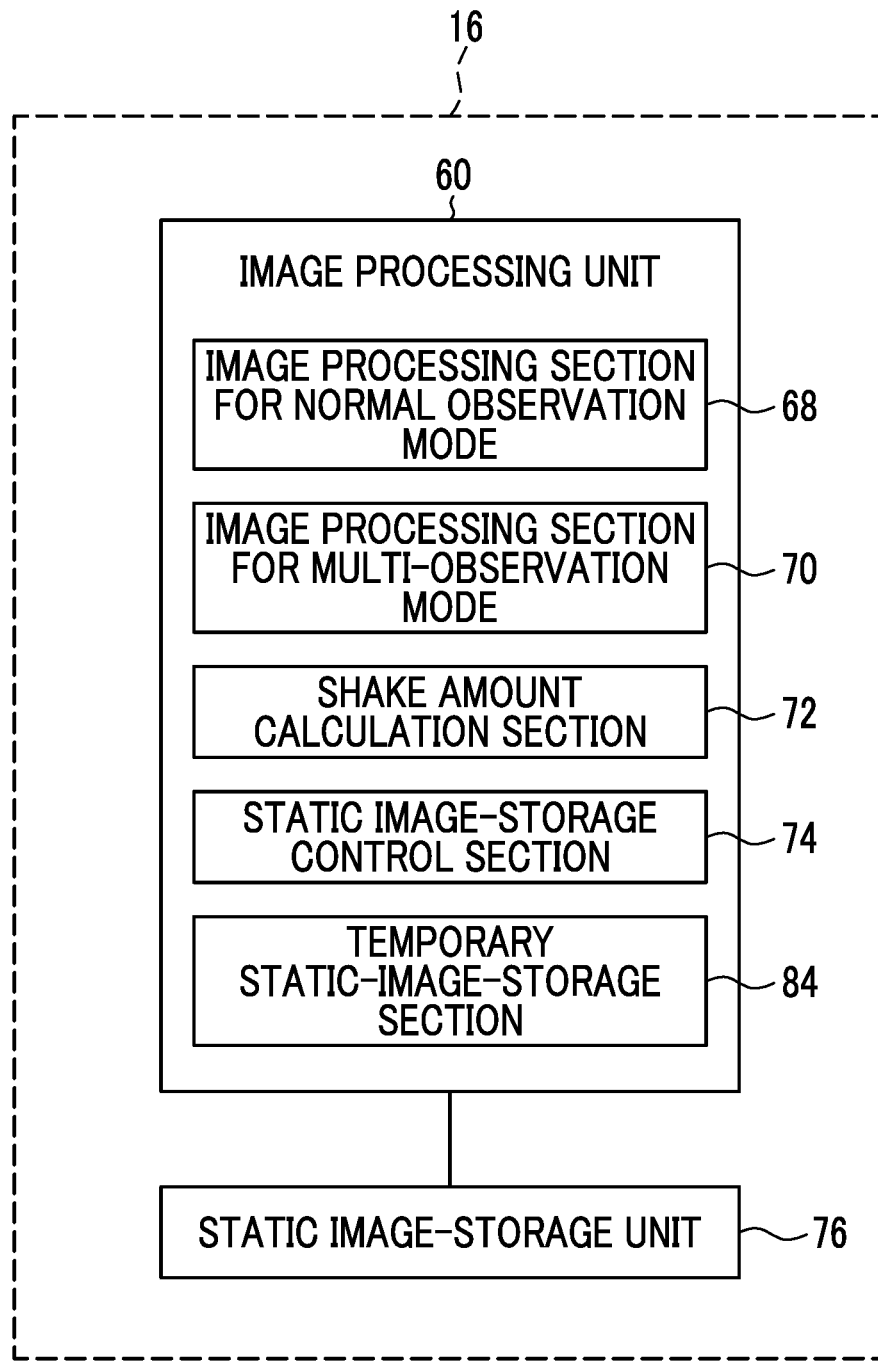
FIG. 16 is a block diagram showing the shake amount calculation section.

As shown in FIG. 16, an image processing unit 60 of this embodiment includes a temporary static-image-storage section 84 in addition to the image processing section 68 for a normal observation mode, the image processing section 70 for a multi-observation mode, the shake amount calculation section 72, and the static image-storage control section 74. In this embodiment, the shake amount-calculation processing section 78 always performs shake amount-calculation processing for images, which are acquired in a specific period dating back from the current point of time, according to settings. A method of calculating a shake amount is the same as those of the first and second embodiments. Accordingly, images acquired in the specific period are regarded as one group, the shake amounts of these images are calculated using parameters varying for each observation mode, the calculated shake amounts are compared with each other, and an image set having a small shake amount is stored in the temporary static-image-storage section 84. A predetermined number of static images for temporary storage, which are the image set having a small shake amount, are stored in the temporary static-image-storage section 84, and the temporary static-image-storage section 84 automatically updates the stored images. Any method can also be employed as a method of storing and updating static images, but a method including storing a predetermined number of static images for temporary storage acquired in the specific period at a specific time interval and deleting the oldest static images for temporary storage, which are acquired at the earliest time, first in a case where new static images for temporary storage are stored is employed in this embodiment. Then, in a case where a static-image-acquisition instruction is given, the temporary static-image-storage section 84 selects static images for temporary storage, which are acquired in the static-image-acquisition instruction period Tr including the time of the static-image-acquisition instruction and the latest time, among the static images for temporary storage, and sends the selected static images for temporary storage to the static image-storage unit 76 as static images for storage.

Figure 17:
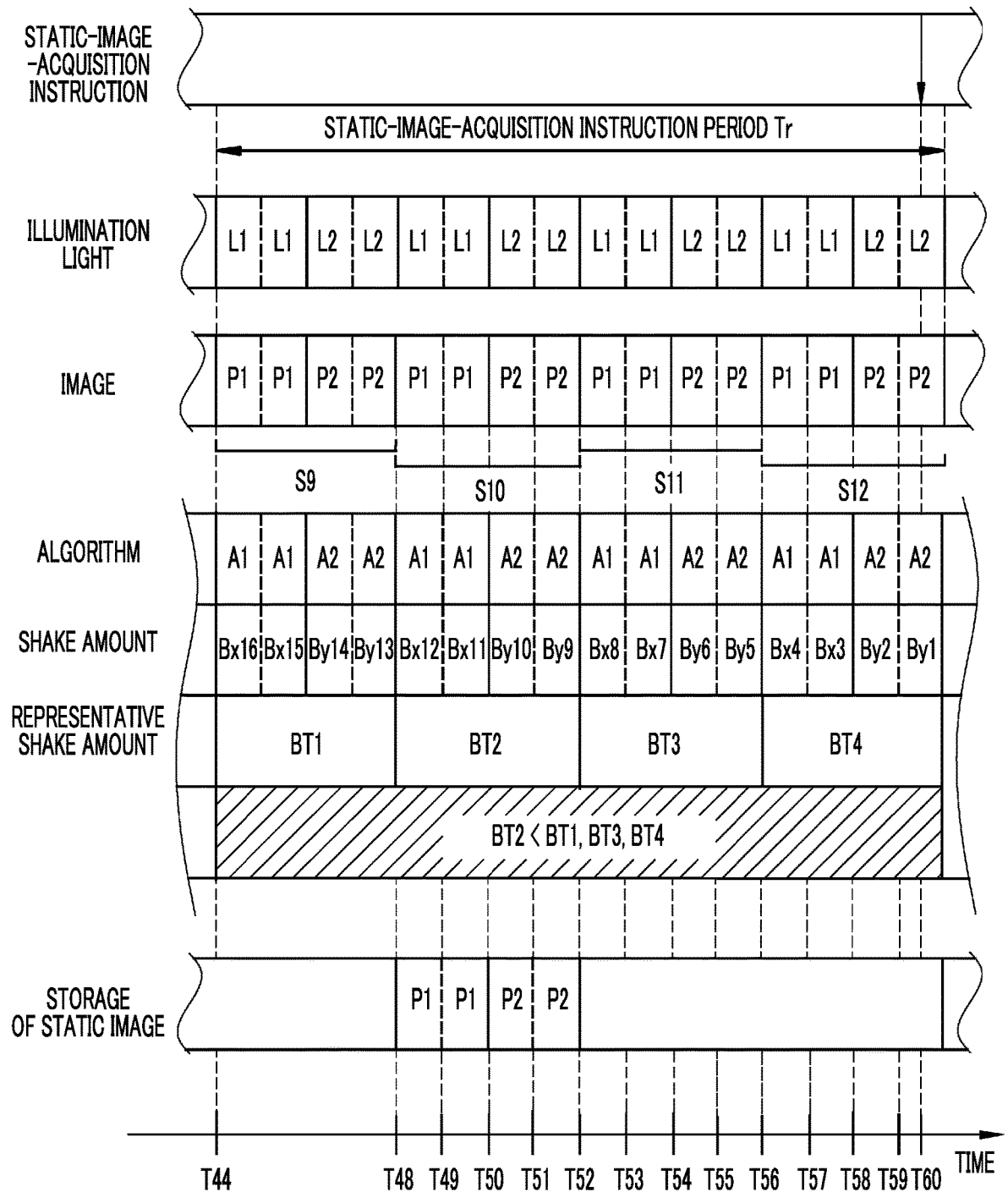

An object for the calculation of shake amounts in this embodiment will be described with reference to FIG. 17. In a case where a static-image-acquisition instruction is given at a timing T60, static images for temporary storage acquired in a static-image-acquisition instruction period Tr including the timing T60, which is the time of the static-image-acquisition instruction, and the latest time are selected among the static images for temporary storage stored in the temporary static-image-storage section 84. A period from a timing T59 to a timing Tn (n is a natural number of 2 or more) is the static-image-acquisition instruction period Tr. The static-image-acquisition instruction period Tr is a period in which four image sets (one image set is formed of images for four frames), that is, images for sixteen frames can be acquired. Accordingly, the static-image-acquisition instruction period Tr is a period from the timing T59 to a timing T44.

As in the first embodiment, even in the static-image-acquisition instruction period Tr, first illumination light L1 and second illumination light L2 are emitted while being switched at an interval of two frames. Further, first images P1 for two frames are obtained according to the emission of the first illumination light for two frames, and second images P2 for two frames are obtained according to the emission of the second illumination light for two frame that is to be emitted after the first illumination light. The acquisition of the first images for two frames and the acquisition of the second images for two frames are alternately performed. Accordingly, an image set S12, which is formed of second images P2 obtained at the timings T58 and T59 and first images P1 obtained at the timings T56 and T57, is obtained in a period from the timing T59 to the timing T56. Likewise, an image set S11, which is formed of second images P2 obtained at the timings T54 and T55 and first images P1 obtained at the timings T52 and T53, is obtained in a period from the timing T55 to the timing T52. Furthermore, an image set S10, which is formed of second images P2 obtained at the timings T50 and T51 and first images P1 obtained at the timings T48 and T49, is obtained. Moreover, an image set S9, which is formed of second images P2 obtained at the timings T46 and T47 and first images P1 obtained at the timings T44 and T45, is obtained.

Then, shake amount-calculation processing is performed on every image of each image set. In this shake amount-calculation processing, the algorithm A1 is applied to the first image and the algorithm A2 is applied to the second image. The algorithm A2 is applied to the second images P2 obtained at the timings T58 and T59 in the case of the image set S12, so that shake amounts By1 and By2 at the timings T58 and T59 are calculated. On the other hand, the algorithm A1 is applied to the first images P1 obtained at the timings T56 and T57, so that shake amounts Bx3 and Bx4 at the timings T56 and T57 are calculated. Likewise, shake amount-calculation processing is performed on every image of the image set S11, so that shake amounts By5, By6, Bx7, and Bx8 are calculated. Further, shake amount-calculation processing is performed on the images of the image set S10, so that shake amounts By9, By10, Bx11, and Bx12 are calculated. Furthermore, shake amount-calculation processing is performed on the images of the image set S9, so that shake amounts By13, By14, Bx15, and Bx16 are calculated.

Next, the static image-storage control section 74 sums up the shake amounts, which are calculated from the every image set, to calculate representative shake amounts. In the case of the image set S12, the static image-storage control section 74 sums up the shake amounts By1, By2, Bx3, and Bx4 to obtain a representative shake amount BT4. Likewise, in the case of the image set S11, the static image-storage control section 74 sums up the shake amounts By5, By6, Bx7, and Bx8 to obtain a representative shake amount BT3. Further, in the case of the image set S10, the static image-storage control section 74 sums up the shake amounts By9, By10, Bx11, and Bx12 to obtain a representative shake amount BT2. Furthermore, in the case of the image set S9, the static image-storage control section 74 sums up the shake amounts By13, By14, Bx15, and Bx16 to obtain a representative shake amount BT1.

Then, the static image-storage control section 74 selects an image set, which has the smallest representative shake amount, among the image sets S9 to S12 as static images for storage. For example, in a case where the representative shake amount BT2 is smallest (BT2<BT1, BT3, and BT4), the image set S10 formed of the second images obtained at the timings T50 and T51 and the first images obtained at the timings T48 and T49 is stored as the static images for temporary storage and is selected as the static images for storage.

In this embodiment, the static image-storage control section 74 calculates a shake amount (a representative shake amount) as a unit of the image set and selects an image set, which has the smallest representative shake amount, as the static images for storage. However, the invention is not limited to this method. For example, among the plurality of images obtained in the specific static-image-acquisition instruction period, a first image having the smallest shake amount with regard to the first images and a second image having the smallest shake amount with regard to the second images may be selected as the static images for storage.

Since static images having a small shake amount are always stored temporarily in this embodiment, a plurality of static images can be stored according to settings and can be used in various ways. For example, static images for temporary storage, which are a plurality of static images having a small shake amount, are continuously displayed, so that images where specific structures are emphasized can be displayed as videos.

In the embodiment, in the multi-observation mode, first illumination light and second illumination light are emitted at an interval of two frames while being switched, and a first observation image corresponding to the first illumination light and a second observation image corresponding to the second illumination light are displayed on the monitor 18 while being switched an interval of two frames. However, three or more kinds of illumination light having wavelength ranges different from each other may be emitted while being switched according to a specific light emission order and a specific light emission period, and three or more kinds of observation images corresponding to the respective kinds of illumination light may be displayed on the monitor 18 while being switched according to a specific display order and a specific display time.

The hardware structures of the processing units, which are included in the processor device 16 in the embodiments, such as the image processing unit 60 and the display control unit 62, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

The invention can be applied to various medical image processing devices in addition to the endoscope systems according to the first to third embodiments.

EXPLANATION OF REFERENCES

10: endoscope system
12: endoscope
12a: insertion part
12b: operation part
12c: bendable part
12d: distal end part
12e: angle knob
13a: static-image-acquisition instruction SW
13b: mode changeover SW
14: light source device
16: processor device
18: monitor
19: keyboard
20: light source unit
20a: V-LED
20b: B-LED
20c: G-LED
20d: R-LED
21: light source control unit
22: light emission period-setting unit
23: optical path-combination unit
26a, 26b: slide bar
27a, 27b: slider
30a: illumination optical system
30b: image pickup optical system
41: light guide
45: illumination lens
46: objective lens
48: image pickup sensor
50: CDS/AGC circuit
52: A/D converter
53: image acquisition unit
56: DSP
58: noise removing unit
60: image processing unit
62: display control unit
66: central control unit
68: image processing section for normal observation mode
70: image processing section for multi-observation mode
72: shake amount calculation section
74: static image-storage control section
76: static image-storage unit
78: shake amount-calculation processing section
80: algorithm switching section
82: temporary video-storage section
84: temporary static-image-storage section

What is claimed is:

1. An endoscope system comprising:
a plurality of semiconductor light sources that emit light having wavelength ranges different from each other;
a light source controller that performs control to cause the plurality of semiconductor light sources to emit a plurality of kinds of illumination light, which include first illumination light having a first light emission ratio and second illumination light having a second light emission ratio different from the first light emission ratio, while switching the plurality of kinds of illumination light according to a specific light emission order and a specific light emission period; and
a processor configured to:
pick up images of an object to be observed illuminated with each illumination light to acquire a plurality of images, the plurality of images including first images obtained using the first illumination light and second images obtained using the second illumination light;
give a static-image-acquisition instruction to acquire static images for storage of the respective images;

calculate shake amounts of the plurality of images acquired in a specific static-image-acquisition instruction period including a timing when the static-image-acquisition instruction is given, in which shake amount-calculation processing for calculating the shake amount varies for each of the images;

perform control to store the plurality of images in a static image-storage as the static images for storage in a case where a specific condition is satisfied with regard to the shake amount;

associate a display condition including a specific display order and a specific display time with the static images for storage, and store the display condition, the specific display order being an order from the first image to the second image, the specific display time being two or more frames for each of the first and second images; and read out the static images for storage and the display condition, and display the static images for storage on a display while switching the static images for storage according to the display condition.

2. The endoscope system according to claim 1, wherein spectral images having a plurality of colors are included in each of the images, and the shake amount-calculation processing includes first shake amount-calculation processing for calculating a first shake amount from a spectral image, which has a first color, of the first images, and second shake amount-calculation processing for calculating a second shake amount from a spectral image, which has a second color different from the first color, of the second images.

3. The endoscope system according to claim 2, wherein the first illumination light includes more light, which has a short wavelength, than the second illumination light, and the first color is a blue color and the second color is a green color.

4. The endoscope system according to claim 1, wherein the processor is configured to store each of a first image having a smallest shake amount with regard to the first images and a second image having a smallest shake amount with regard to the second images, among the plurality of images obtained in the specific static-image-acquisition instruction period, as the static images for storage.

5. The endoscope system according to claim 1, wherein the shake amount-calculation processing differs depending on an observation mode in which an image, which is an object of which the shake amount is to be calculated, is acquired.

6. The endoscope system according to claim 3, wherein the first shake amount-calculation processing is a first algorithm for calculating the shake amount using a blue spectral image, and the second shake amount-calculation processing is a second algorithm for calculating the shake amount using a green spectral image.

* * * * *